(12) United States Patent
Barrett et al.

(10) Patent No.: US 6,469,004 B1
(45) Date of Patent: Oct. 22, 2002

(54) BENZOHETEROCYCLES AND THEIR USES AS MEK INHIBITORS

(75) Inventors: Stephen Barrett, Livonia, MI (US); Haile Tecle, Ann Arbor, MI (US); Alexander J. Bridges, Saline, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/889,059

(22) PCT Filed: Dec. 21, 2000

(86) PCT No.: PCT/US99/30483

§ 371 (c)(1), (2), (4) Date: Jul. 11, 2001

(87) PCT Pub. No.: WO00/42022

PCT Pub. Date: Jul. 20, 2000

Related U.S. Application Data

(60) Provisional application No. 60/115,873, filed on Jan. 13, 1999, and provisional application No. 60/122,553, filed on Mar. 2, 1999.

(51) Int. Cl.[7] ............... C07D 235/06; A61K 31/4184
(52) U.S. Cl. ............... 514/248; 544/353; 548/126; 548/178; 548/217; 548/261; 548/309.7; 514/248; 514/359; 514/361; 514/362; 514/367; 514/375; 514/387
(58) Field of Search ............... 548/309.7, 126, 548/178, 217, 261; 544/353; 514/248, 359, 361, 362, 367, 375, 387

(56) References Cited

U.S. PATENT DOCUMENTS

| | | | |
|---|---|---|---|
| 5,525,625 A | 6/1996 | Bridges | |
| 6,310,060 B1 | 10/2001 | Barrett et al. | |

FOREIGN PATENT DOCUMENTS

| | | |
|---|---|---|
| WO | WO98/37881 | 9/1998 |
| WO | WO99/01426 | 1/1999 |

OTHER PUBLICATIONS

PCT International Search Report, PCT/US99/30483, May 23, 2000.

*Primary Examiner*—Robert Gerstl
(74) *Attorney, Agent, or Firm*—Evelyn D. Shen; Suzanne M. Harvey

(57) ABSTRACT

The invention provides compounds having formula (I), wherein W is OH, or derivatives of the carboxylic acid, and Q is a heterocyclo-condensed ortho-phenylene residue. These compounds are useful as MEK inhibitors, particularly in the treatment of proliferative diseases such as cancer.

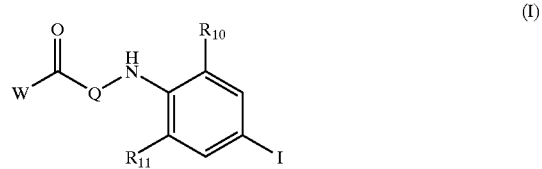

44 Claims, No Drawings

BENZOHETEROCYCLES AND THEIR USES AS MEK INHIBITORS

This application is a 371 application of PCT/US99/30483 filed Dec. 21, 1999, which claims benefit of priority to U.S. provisional application Serial No. 60/115,873 filed Jan. 13, 1999 and U.S. provisional application Serial No. 60/122,553 filed Mar. 2, 1999.

BACKGROUND

MEK enzymes are dual specificity kinases involved in, for example, immunomodulation, inflammation, and proliferative diseases such as cancer and restenosis.

Proliferative diseases are caused by a defect in the intracellular signaling system, or the signal transduction mechanism of certain proteins. Defects include a change either in the intrinsic activity or in the cellular concentration of one or more signaling proteins in the signaling cascade. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, a G-protein that is activated when bound to GTP, and inactivated when bound to GDP. The above-mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras-GTP complex, are common in cancers, and lead to the signaling cascade below Ras being chronically activated.

Activated Ras leads in turn to the activation of a cascade of serine/threonine kinases. One of the groups of kinases known to require an active Ras-GTP for its own activation is the Raf family. These in turn activate MEK (e.g., $MEK_1$ and $MEK_2$) which then activates MAP kinase, ERK ($ERK_1$ and $ERK_2$). Activation of MAP kinase by mitogens appears to be essential for proliferation; constitutive activation of this kinase is sufficient to induce cellular transformation. Blockade of downstream Ras signaling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold. Activated MAP kinase can then catalyze the phosphorylation of a large number of proteins, including several transcription factors and other kinases. Many of these MAP kinase phosphorylations are mitogenically activating for the target protein, such as a kinase, a transcription factor, or another cellular protein. In addition to Raf-1 and MEKK, other kinases activate MEK, and MEK itself appears to be a signal integrating kinase. Current understanding is that MEK is highly specific for the phosphorylation of MAP kinase. In fact, no substrate for MEK other than the MAP kinase, ERK, has been demonstrated to date and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

SUMMARY

The invention features a compound having the formula (1) below:

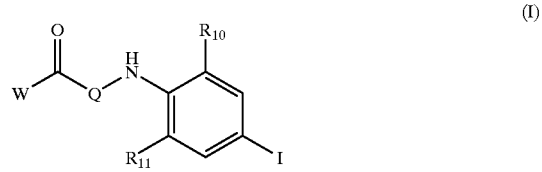

(I)

In formula (I), W is $OR_1$, $NR_2OR_1$, $NR_AR_B$, $NR_2NR_AR_B$, $O(CH_2)_{2-4}NR_AR_B$, or $NR_2(CH_2)_{2-4}NR_AR_B$. $R_1$ is H, $C_{1-8}$ alkyl, $C_{3-8}$ alkenyl, $C_{3-8}$ alkynyl, $C_{3-8}$ cycloalkyl, phenyl, (phenyl)$C_{1-4}$ alkyl, (phenyl)$C_{3-4}$ alkenyl, (phenyl)$C_{3-4}$ alkynyl, ($C_{3-8}$ cycloalkyl)$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical)$C_{1-4}$ alkyl, ($C_{3-8}$ heterocyclic radical)$C_{3-4}$ alkenyl, ($C_{3-8}$ heterocyclic radical)$C_{3-4}$ alkynyl or $(CH_2)_{2-4}NR_CR_D$. $R_2$ is H, $C_{1-4}$ alkyl, phenyl, $C_{3-6}$ cycloalkyl, $C_{3-6}$ heterocyclic radical, or ($C_{3-6}$ cycloalkyl) methyl. $R_A$ is H, $C_{1-6}$ alkyl, $C_{3-8}$ alkenyl, $C_{3-8}$ alkynyl, $C_{3-8}$ cycloalkyl, phenyl, ($C_{3-8}$ cycloalkyl)$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical)$C_{1-4}$ alkyl, (aminosulfonyl)phenyl, [(aminosulfonyl)phenyl]$C_{1-4}$ alkyl, (aminosulfonyl)$C_{1-6}$ alkyl, (aminosulfonyl)$C_{3-6}$ cycloalkyl, [(aminosulfonyl)$C_{3-6}$ cycloalkyl]$C_{1-4}$ alkyl, or $(CH_2)_{2-4}NR_CR_D$. $R_B$ is H, $C_{1-8}$ alkyl, $C_{3-8}$ alkenyl, $C_{3-8}$ alkynyl, $C_{3-8}$ cycloalkyl, or phenyl.

Q is one of the following formulae (i)–(iii):

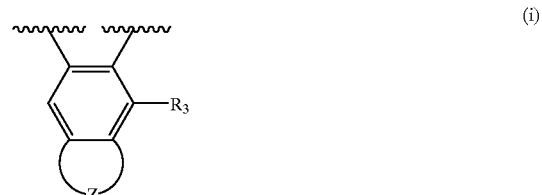

(i)

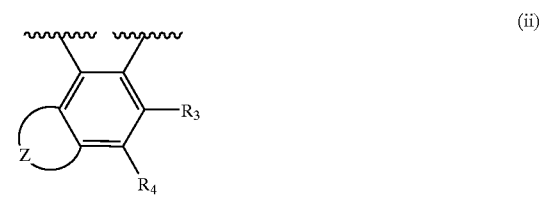

(ii)

-continued (iii)

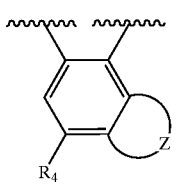

$R_3$ is H or F; $R_4$ is halo, $NO_2$, $SO_2NR_O(CH_2)_{2-4}NR_ER_F$, $SO_2NR_ER_F$ or (CO)T. T is $C_{1-8}$ alkyl, $C_{3-8}$ cycloalkyl, $(NR_ER_F)C_{1-4}$ alkyl, $OR_F$, $—NR_O(CH_2)_{2-4}$ $NR_ER_F$, or $NR_ER_F$; Z is one of the following formulae (iv)–(viii):

(iv)

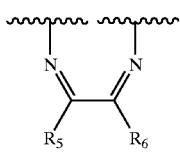

(v)

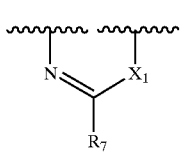

(vi)

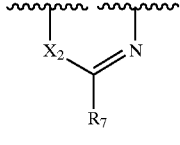

(vii)

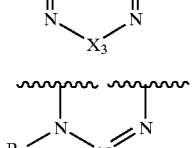

(viii)

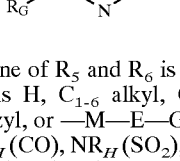

One of $R_5$ and $R_6$ is H or methyl and the other of $R_5$ and $R_6$ is H, $C_{1-6}$ alkyl, $C_{2-6}$ alkenyl, $C_{2-6}$ alkynyl, phenyl, benzyl, or —M—E—G. M is O, CO, $SO_2$, $NR_J$, $(CO)NR_H$, $NR_H(CO)$, $NR_H(SO_2)$, $(SO_2)NR_H$, or $CH_2$. E is $(CH_2)_{1-4}$ or $(CH_2)_mO(CH_2)_p$ where $1 \leq$ (each of m and p) $\leq 3$ and $2 \leq (m+p) \leq 4$; or E is absent. G is $R_K$, $OR_J$, or $NR_JR_K$, provided that if p=1, then G is H. $R_7$ is H, $C_{1-4}$ alkyl, $C_{2-4}$ alkenyl, $C_{2-4}$ alkynyl, $C_{3-6}$ cycloalkyl, phenyl, 2-pyridyl, 3-pyridyl, 4-pyridyl, $(CH_2)_{1-2}Ar$, where Ar is phenyl, 2-pyridyl, 3-pyridyl, or 4-pyridyl, $SO_2NR_H(CH_2)_{2-4}NR_JR_K$, (CO)$(CH_2)_{2-4}NR_JR_K$ or $(CO)NR_H(CH_2)_{2-4}NR_JR_K$. $X_1$ is O, S, $NR_8$, or $CHR_9$; $X_2$ is O, S, or $CHR_9$; and $X_3$ is O or S. In one embodiment, if $X_1$ or $X_2$ is $CHR_9$, the disclosed compound may also be a tautomerized indole. $R_8$ is H, $C_{1-4}$ alkyl, phenyl, 2-pyridyl, 3-pyridyl, 4-pyridyl, $(CH_2)_{1-2}Ar$, where Ar is phenyl, 2-pyridyl, 3-pyridyl, or 4-pyridyl, $C_{2-4}$ alkenyl, $C_{2-4}$ alkynyl, $C_{3-6}$ cycloalkyl, or ($C_{2-4}$ alkyl)$NR_LR_M$ provided $R_7$ and $R_8$ together have no more than 14 carbon atoms, exclusive of $R_L$, $R_M$, $R_J$ and $R_K$. $R_G$ is $C_{1-4}$ alkyl, phenyl, 2-pyridyl, 3-pyridyl, 4-pyridyl, $C_{3-4}$ alkenyl, $C_{3-4}$ alkynyl, $C_{3-6}$ cycloalkyl, (CO)$OR_P$, ($C_{2-4}$ alkyl)$NR_LR_M$, (CO)$NR_N(CH_2)_{2-4}NR_LR_M$, (CO)$NR_LR_M$, (CO)$(CH_2)_{2-4}$-$NR_LR_M$, or $(CH_2)_{1-2}Ar$, where Ar is phenyl, 2-pyridyl, 3-pyridyl, or 4-pyridyl. $R_9$ is $C_{1-4}$ alkyl, phenyl, 2-pyridyl, 3-pyridyl, 4-pyridyl, $C_{2-4}$ alkenyl, $C_{2-4}$ alkynyl, $C_{3-6}$ cycloalkyl, (CO)$OR_P$, ($C_{2-4}$ alkyl)$NR_LR_M$, (CO)$NR_N(CH_2)_{2-4}NR_LR_M$, (CO)$NR_LR_M$, (CO)$(CH_2)_{2-4}$—$NR_LR_M$, or $(CH_2)_{1-2}Ar'$, where Ar' is phenyl, 2-pyridyl, 3-pyridyl, or 4-pyridyl. $R_P$ is H, $C_{1-6}$ alkyl, phenyl, $C_{3-4}$ alkenyl, $C_{3-4}$ alkynyl, $C_{3-6}$ cycloalkyl, or $(CH_2)_{2-4}NR_LR_M$; $R_{10}$ is H, methyl, halo, or $NO_2$; $R_{11}$ is H, methyl, halo, or $NO_2$. Each of $R_C$, $R_D$, $R_E$, $R_F$, $R_I$, $R_J$, $R_K$, $R_L$ and $R_M$ is independently selected from H, $C_{1-4}$ alkyl, $C_{3-4}$ alkenyl, $C_{3-4}$ alkynyl, $C_{3-6}$ cycloalkyl, and phenyl; each of $NR_CR_D$, $NR_ER_F$, $NR_JR_K$, and $NR_LR_M$ can also independently be morpholinyl, piperazinyl, pyrrolidinyl, or piperadinyl. Each of $R_H$, $R_N$, and $R_O$ is independently H, methyl, or ethyl. Finally, each hydrocarbon radical or heterocyclic radical above is optionally substituted with between 1 and 3 substituents independently selected from halo, $C_{1-4}$ alkyl, $C_{3-6}$ cycloalkyl, $C_{2-4}$ alkenyl, $C_{2-4}$ alkynyl, phenyl, hydroxyl, amino, (amino)sulfonyl, and $NO_2$, wherein each substituent alkyl, cycloalkyl, alkenyl, alkynyl or phenyl is in turn optionally substituted with between 1 and 3 substituents independently selected from halo, $C_{1-2}$ alkyl, hydroxyl, amino, and $NO_2$. In addition to the above compounds, the invention also provides a pharmaceutically-acceptable salt or $C_{1-7}$ ester thereof.

The invention also relates to a pharmaceutical composition including (a) a benzoheterocycle (e.g., of formula I) and (b) a pharmaceutically-acceptable carrier.

The invention further relates to methods for treating proliferative diseases, such as cancer, restenosis, psoriasis, autoimmune disease, and atherosclerosis. Other aspects of the invention include methods for treating MEK-related (including ras-related) cancers, whether solid or hematopoietic. Examples of cancers include colorectal, cervical, breast, ovarian, brain, acute leukemia, gastric, non-small cell lung, pancreatic and renal cancer. Further aspects of the invention include methods for treating or reducing the symptoms of xenograft (cell(s), organ, limb, skin, or bone marrow transplant) rejection, osteoarthritis, rheumatoid arthritis, cystic fibrosis, complications of diabetes (including diabetic retinopathy and diabetic nephropathy), hepatomegaly, cardiomegaly, stroke (such as acute focal ischemic stroke and global cerebral ischemia), heart failure, septic shock, asthma, and Alzheimer's disease. Compounds of the invention are also useful as antiviral agents for treating viral infections such as HIV, hepatitis (B) virus (HBV), human papilloma virus (HPV), cytomegalovirus (CMV), and Epstein-Barr virus (EBV). These methods include the step of administering to a patient in need of such treatment, or suffering from such a disease or condition, a pharmaceutically-effective amount of a disclosed compound or pharmaceutical composition thereof. Preferably, in the above methods of treatment, the compound of the invention is a selective MEK inhibitor.

The invention also features methods of combination therapy, such as a method for treating cancer, wherein the method further includes providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil (5FU), flutamide, and gemcitabine.

The chemotherapy or radiation therapy may be administered before, concurrently, or after the administration of a disclosed compound according to the needs of the patient.

The invention also features synthetic methods and synthetic intermediates disclosed herein.

Other aspects of the invention are provided in the description, examples, and claims below.

DETAILED DESCRIPTION

The invention features benzoheterocycle compounds, pharmaceutical compositions thereof, and methods of using such compounds and compositions.

According to one aspect of the invention, the compounds are MEK inhibitors. MEK inhibition assays include the cascade assay for inhibitors of MAP kinase pathway described at column 6, line 36 to column 7, line 4 of U.S. Pat. No. 5,525,625 and the in vitro MEK assay at column 7, lines 4–27 of the same patent, the entire disclosure of which is incorporated by reference (see also Examples 22–25 below).

A. TERMS

Certain terms are defined below and by their usage throughout this disclosure.

Alkyl groups include aliphatic (i.e., hydrocarbyl or hydrocarbon radical structures containing hydrogen and carbon atoms) with a free valence. Alkyl groups are understood to include straight chain and branched structures. Examples include methyl, ethyl, propyl, isopropyl, butyl, n-butyl, isobutyl, t-butyl, pentyl, isopentyl, 2,3-dimethylpropyl, hexyl, 2,3-dimethylhexyl, 1,1-dimethylpentyl, heptyl, and octyl. Cycloalkyl groups include cyclopropyl, cyclobutyl, cyclopentyl, cyclohexyl, cycloheptyl, and cyclooctyl.

Alkyl groups can be substituted with 1, 2, 3 or more substituents which are independently selected from halo (fluoro, chloro, bromo, or iodo), hydroxy, amino, alkoxy, alkylamino, dialkylamino, cycloalkyl, aryl, aryloxy, arylalkyloxy, heterocyclic radical, and (heterocyclic radical)oxy. Specific examples include fluoromethyl, hydroxyethyl, 2,3-dihydroxyethyl, (2- or 3-furanyl)methyl, cyclopropylmethyl, benzyloxyethyl, (3-pyridinyl)methyl, (2- or 3-furanyl)methyl, (2-thienyl)ethyl, hydroxypropyl, aminocyclohexyl, 2-dimethylaminobutyl, methoxymethyl, N-pyridinylethyl, diethylaminoethyl, and cyclobutylmethyl.

Alkenyl groups are analogous to alkyl groups, but have at least one double bond (two adjacent $Sp^2$ carbon atoms). Depending on the placement of a double bond and substituents, if any, the geometry of the double bond may be entgegen (E), or zusammen (Z), cis, or trans. Similarly, alkynyl groups have at least one triple bond (two adjacent sp carbon atoms). Unsaturated alkenyl or alkynyl groups may have one or more double or triple bonds, respectively, or a mixture thereof; like alkyl groups, unsaturated groups may be straight chain or branched, and they may be substituted as described both above for alkyl groups and throughout the disclosure by example. Examples of alkenyls, alkynyls, and substituted forms include cis-2-butenyl, trans-2-butenyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4-hydroxy-3-butynyl, 3-(3-fluorophenyl)-2-propynyl, and 2-methyl-2-propenyl. In formula (I), alkenyl and alkynyl groups can be, for example, $C_{2-4}$ or $C_{2-8}$, and are preferably $C_{3-4}$ or $C_{3-8}$.

More general forms of substituted hydrocarbon radicals include hydroxyalkyl, hydroxyalkenyl, hydroxyalkynyl, hydroxycycloalkyl, hydroxyaryl, and corresponding forms for the prefixes amino-, halo- (e.g., fluoro-, chloro-, or bromo-), nitro-, alkyl-, phenyl-, cycloalkyl- and so on, or combinations of substituents. According to formula (I), therefore, substituted alkyls include hydroxyalkyl, aminoalkyl, nitroalkyl, haloalkyl, alkylalkyl (branched alkyls, such as methylpentyl), (cycloalkyl)alkyl, phenylalkyl, alkoxy, alkylaminoalkyl, dialkylaminoalkyl, arylalkyl, aryloxyalkyl, arylalkyloxyalkyl, (heterocyclic radical)alkyl, and (heterocyclic radical)oxyalkyl. $R_1$ thus includes hydroxyalkyl, hydroxyalkenyl, hydroxyalkynyl, hydroxycycloalkyl, hydroxyaryl, aminoalkyl, aminoalkenyl, aminoalkynyl, aminocycloalkyl, aminoaryl, alkylalkenyl, (alkylaryl)alkyl, (haloaryl)alkyl, (hydroxyaryl)alkynyl, and so forth. Similarly, $R_A$ includes hydroxyalkyl and aminoaryl, and $R_B$ includes hydroxyalkyl, aminoalkyl, and hydroxyalkyl(heterocyclic radical)alkyl.

Heterocyclic radicals, which include but are not limited to heteroaryls, include: furyl, oxazolyl, isoxazolyl, thiophenyl, thiazolyl, pyrrolyl, imidazolyl, 1,3,4-triazolyl, tetrazolyl, pyridinyl, pyrimidinyl, pyridazinyl, indolyl, and their non-aromatic counterparts. Further examples of heterocyclic radicals include piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, and octahydrobenzofuranyl.

Selective MEK 1 or MEK 2 inhibitors are those compounds which inhibit the MEK 1 or MEK 2 enzymes, respectively, without substantially inhibiting other enzymes such as MKK3, PKC, Cdk2A, phosphorylase kinase, EGF, and PDGF receptor kinases, and C-src. In general, a selective MEK 1 or MEK 2 inhibitor has an $IC_{50}$ for MEK 1 or MEK 2 that is at least one-fiftieth (1/50) that of its $IC_{50}$ for one of the above-named other enzymes. Preferably, a selective inhibitor has an $IC_{50}$ that is at least 1/100, more preferably 1/500, and even more preferably 1/1000, 1/5000, or less than that of its $IC_{50}$ or one or more of the above-named enzymes.

B. COMPOUNDS

One aspect of the invention features disclosed compounds shown in formula (I) in the Summary section. Embodiments of the invention includes compounds of formula (I) wherein: (a) Q is formula (i); (b) $R_3$ is H or fluoro; (c) $R_4$ is fluoro, chloro, or bromo; (d) $R_{10}$ is H, methyl, fluoro, or chloro; (e) $R_{11}$ is methyl, chloro, fluoro, nitro, or hydrogen; (f) $R_{11}$ is H; (g) $R_{11}$ is fluoro; (h) each of $R_{10}$ and $R_{11}$ is fluoro; (i) $R_1$ is H, methyl, ethyl, propyl, isopropyl, isobutyl, benzyl, phenethyl, allyl, $C_{3-5}$ alkenyl, $C_{3-6}$ cycloalkyl, ($C_{3-5}$ cycloalkyl)$C_{1-2}$ alkyl, ($C_{3-5}$ heterocyclic radical)$C_{1-2}$ alkyl, or $(CH_2)_{2-4}NR_CR_D$; (j) $R_1$ is H or ($C_{3-4}$ cycloalkyl)$C_{1-2}$ alkyl; (k) $R_2$ is H or methyl; (l) $R_A$ has at least one hydroxyl substituent; (m) $R_A$ is H, methyl, ethyl, isobutyl, hydroxyethyl, phenyl, 2-piperidin-1-yl-ethyl, 2,3-dihydroxy-propyl, 3-[4-(2-hydroxyethyl)-piperazin-1-yl]-propyl, 2-pyrrolidin-1-yl-ethyl, or 2-diethylamino-ethyl; and $R_B$ is H; or where $R_B$ is methyl and $R_A$ is phenyl.; (n) W is $NR_AR_B$ or $NR_2NR_AR_B$; (o) W is $NR_2(CH_2)_{2-4}NR_AR_B$ or $O(CH_2)_{2-3}NR_AR_B$; (p) W is $NR_2OR_1$; (q) W is $OR_1$; (r) Z is formula (v); or (s) $X_1$ is $NR_8$, and $R_7$ is H; or (t) combinations thereof. In formula (I), the values for Z are shown left to right, or in a counter-clockwise orientation around the phenyl ring of Q.

According to one aspect of the invention, the compound of formula (I) has a structure wherein: Q is formula (i) or (ii); $R_3$ is H or fluoro; $R_4$ is fluoro, chloro, or bromo; $R_{10}$ is H, methyl, or chloro; $R_{11}$, is chloro, fluoro, or hydrogen; $R_1$ is H, methyl, ethyl, propyl, isopropyl, isobutyl, benzyl, phenethyl, allyl, $C_{3-5}$ alkenyl, $C_{3-6}$ cycloalkyl, ($C_{3-5}$ cycloalkyl)$C_{1-2}$ alkyl, ($C_{3-5}$ heterocyclic radical)$C_{1-2}$ alkyl, or $(CH_2)_{2-4}NR_CR_D$; $R_1$ is H or ($C_{3-4}$ cycloalkyl)$C_{1-2}$ alkyl; $R_2$ is H or methyl; and Z is formula (v) or (vi). One embodiment of this aspect, $X_1$ is $NR_8$. An example would be 7-fluoro-6-(4-iodo-2-methyl-phenylamino)-1[(2'- morpholinyl)-ethyl]-2-(phenyl)-benzoimidazole-5-carboxylic acid cyclopropylmethoxy-amide.

Embodiments of the invention also include compounds wherein $R_{10}$ is H; $R_{10}$ is methyl or chloro; and where $R_{10}$ is chloro. In some embodiments, $R_7$ and $R_8$ together have no more than 14 carbon atoms, exclusive of $R_L$, $R_M$, $R_J$ and $R_K$. Examples of this include compounds wherein $R_7$ and $R_8$ together have no more than 13 carbon atoms; no more than 7, 8, or 10 carbon atoms; between 4 and 8 carbon atoms; between 1 and 10 carbon atoms; between 1 and 8 carbon atoms; and no more than 6 carbon atoms.

Preferably, where one of $R_1$, $R_2$, $R_A$, $R_B$, $R_C$, $R_D$, $R_E$, $R_F$, $R_I$, $R_J$, $R_K$, $R_L$, $R_M$, $R_G$, $R_H$, $R_N$, $R_O$, and $R_P$ is an alkenyl or alkynyl group, its double or triple bond, respectively, is not adjacent the point of attachment. For example, where W is $NR_2OR_1$, $R_2$ is preferably prop-2-ynyl, or but-2 or 3-enyl, and less preferably prop-1-ynyl or but-1-enyl.

Listed below are some of the preferred structures which can be synthesized utilizing Schemes 1, 2, 10, and 11. Free acids, free hydroxamic acids, and cyclopropylmethyl hydroxamates are grouped together. For example, compounds 1, 11, and 21 differ only by "W" (as defined in the claims); compounds 2, 12, and 22 are similarly related. Preferred compounds also include the 2-chloro (replacing 2-methyl) analogs of the listed compounds.

Examples of compounds include: 7-Fluoro-6-(4-iodo-2-methyl-phenylamino)-1H-benzoimidazole-5-carboxylic acid (APK $IC_{50}$=47±17 nM); 7-Fluoro-6-(4-iodo-2-methyl-phenylamino)-benzooxazole-5-carboxylic acid; 7-Fluoro-6-(4-iodo-2-methyl-phenylamino)-benzothiazole-5-carboxylic acid; 7-Fluoro-6-(4-iodo-2-methyl-phenylamino)-benzo[1,2,5]thiadiazole-5-carboxylic acid; 7-Fluoro-6-(4-iodo-2-methyl-phenylamino)-benzo[1,2,5]oxadiazole-5-carboxylic acid; 7-Fluoro-6-(4-iodo-2-methyl-phenylamino)-2-(2-hydroxyethyl)-1H-benzoimidazole-5-carboxylic acid; 7-Fluoro-6-(4-iodo-2-methyl-phenylamino)-2-(2-dimethylamino-ethyl)-1H-benzoimidazole-5-carboxylic acid; 7-Fluoro-6-(4-iodo-2-methyl-phenylamino)-1-acetyl-benzoimidazole-5-carboxylic acid; 8-Fluoro-7-(4-iodo-2-methyl-phenylamino)-quinoxaline-6-carboxylic acid; 7-Fluoro-6-(4-iodo-2-methyl-phenylamino)-1H-benzotriazole-5-carboxylic acid; 7-Fluoro-6-(4-iodo-2-methyl-phenylamino)-1H-benzoimidazole-5-carboxylic acid hydroxyamide; 7-Fluoro-6-(4-iodo-2-methyl-phenylamino)-benzooxazole-5-carboxylic acid hydroxyamide; 7-Fluoro-6-(4-iodo-2-methyl-phenylamino)-benzothiazole-5-carboxylic acid hydroxyamide; 7-Fluoro-6-(4-iodo-2-methyl-phenylamino)-benzo[1,2,5]thiadiazole-5-carboxylic acid hydroxyamide; 7-Fluoro-6-(4-iodo-2-methyl-phenylamino)-benzo[1,2,5]oxadiazole-5-carboxylic acid hydroxyamide; 7-Fluoro-6-(4-iodo-2-methyl-phenylamino)-2-(2-hydroxyethyl)-1H-benzoimidazole-5-carboxylic acid hydroxyamide; 7-Fluoro-6-(4-iodo-2-methyl-phenylamino)-2-(2-dimethylamino-ethyl)-1H-benzoimidazole-5-carboxylic acid hydroxyamide; 7-Fluoro-6-(4-iodo-2-methyl-phenylamino)-1-acetyl-benzoimidazole-5-carboxylic acid hydroxyamide; 8-Fluoro-7-(4-iodo-2-methyl-phenylamino)-quinoxaline-6-carboxylic acid hydroxyamide; 7-Fluoro-6-(4-iodo-2-methyl-phenylamino)-1H-benzotriazole-5-carboxylic acid hydroxyamide; 7-Fluoro-6-(4-iodo-2-methyl-phenylamino)-1H-benzoimidazole-5-carboxylic acid cyclopropylmethoxy-amide; 7-Fluoro-6-(4-iodo-2-methyl-phenylamino)-benzooxazole-5-carboxylic acid cyclopropylmethoxy-amide; 7-Fluoro-6-(4-iodo-2-methyl-phenylamino)-benzothiazole-5-carboxylic acid cyclopropylmethoxy-amide; 7-Fluoro-6-(4-iodo-2-methyl-phenylamino)-benzo[1,2,5]thiadiazole-5-carboxylic acid cyclopropylmethoxy-amide; 7-Fluoro-6-(4-iodo-2-methyl-phenylamino)-benzo[1,2,5]oxadiazole-5-carboxylic acid cyclopropylmethoxy-amide; 7-Fluoro-6-(4-iodo-2-methyl-phenylamino)-2-(2-hydroxyethyl)-1H-benzoimidazole-5-carboxylic acid cyclopropylmethoxy-amide; 7-Fluoro-6-(4-iodo-2-methyl-phenylamino)-2-(2-dimethylamino-ethyl)-1H-benzoimidazole-5-carboxylic acid cyclopropylmethoxy-amide; 7-Fluoro-6-(4-iodo-2-methyl-phenylamino)-1-acetyl-benzoimidazole-5-carboxylic acid cyclopropylmethoxy-amide; 8-Fluoro-7-(4-iodo-2-methyl-phenylamino)-quinoxaline-6-carboxylic acid cyclopropylmethoxy-amide; and 7-Fluoro-6-(4-iodo-2-methyl-phenylamino)-1H-benzotriazole-5-carboxylic acid cyclopropylmethoxy-amide The following is a list of examples representing schemes 3–9. As above, free acids, free hydroxamic acids, and cyclopropylmethyl hydroxamates are grouped together. For example, compounds 31, 45, and 59 differ only by "W" (as defined in the claims); compounds 32, 46, and 60 are similarly related. Preferred compounds also include the 2-chloro (replacing 2-methyl) analogs of the listed compounds.

Examples of compounds from schemes 3–9 include: 4-Fluoro-5-(4-iodo-2-methyl-phenylamino)-benzothiazole-6-carboxylic acid; 4-Fluoro-5-(4-iodo-2-methyl-phenylamino)-benzooxazole-6-carboxylic acid; 5-(2-Chloro-4-iodo-phenylamino)-6,7-difluoro-3H-benzoimidazole4-carboxylic acid; 6,7-Difluoro-2-(2-hydroxy-ethyl)-5-(4-iodo-2-methyl-phenylamino)-3H-benzoimidazole-4-carboxylic acid; 6,7-Difluoro-5-(4-iodo-2-methyl-phenylamino)-benzooxazole-4-carboxylic acid; 6,7-Difluoro-5-(4-iodo-2-methyl-phenylamino)-benzothiazole-4-carboxylic acid; 7,8-Difluoro-6-(4-iodo-2-methyl-phenylamino)-quinoxaline-5-carboxylic acid; 6-(4-Iodo-2-methyl-phenylamino)-8-nitro-quinoxaline-5-carboxylic acid; 5-(4-Iodo-2-methyl-phenylamino)-8-nitro-quinoxaline-6-carboxylic acid; 8-Chloro-5-(4-iodo-2-methyl-phenylamino)-quinoxaline-6-carboxylic acid; 3-Cyclopropyl-7-(4-iodo-2-methyl-phenylamino)-3H-benzoimidazole4,6-dicarboxylic acid 4-dimethylamide; 7-Bromo-4-(4-iodo-2-methyl-phenylamino)-benzooxazole-5-carboxylic acid; 7-(2-Chloro-4-iodo-phenylamino)-4-fluoro-benzothiazole-6-carboxylic acid; 7-(4-Iodo-2-methyl-phenylamino)-4-nitro-benzooxazole-6-carboxylic acid; 4-Fluoro-5-(4-iodo-2-methyl-phenylamino)-benzothiazole-6-carboxylic acid hydroxyamide; 4-Fluoro-5-(4-iodo-2-methyl-phenylamino)-benzooxazole-6-carboxylic acid hydroxyamide; 5-(2-Chloro-4-iodo-phenylamino)-6,7-difluoro-3H-benzoimidazole-4-carboxylic acid hydroxyamide; 6,7-Difluoro-2-(2-hydroxy-ethyl)-5-(4-iodo-2-methyl-phenylamino)-3H-benzoimidazole-4-carboxylic acid hydroxyamide; 6,7-Difluoro-5-(4-iodo-2-methyl-phenylamino)-benzooxazole-4-carboxylic acid hydroxyamide; 6,7-Difluoro-5-(4-iodo-2-methyl-phenylamino)-benzothiazole-4-carboxylic acid hydroxyamide; 7,8-Difluoro-6-(4-iodo-2-methyl-phenylamino)-quinoxaline-5-carboxylic acid hydroxyamide; 6-(4-Iodo-2-methyl-phenylamino)-8-nitro-quinoxaline-5-carboxylic acid hydroxyamide; 5-(4-Iodo-2-methyl-phenylamino)-8-nitro-quinoxaline-6-carboxylic acid hydroxyamide; 8-Chloro-5-(4-iodo-2-methyl-phenylamino)-quinoxaline-6-carboxylic acid hydroxyamide; 3-Cyclopropyl-7-(4-iodo-2-methyl-phenylamino)-3H-benzoimidazole-4,6-dicarboxylic acid 4-dimethylamide 6-hydroxyamide; 7-Bromo-4-(4-iodo-2-methyl-phenylamino)-benzooxazole-5-carboxylic acid hydroxyamide; 7-(2-Chloro-4-iodo-phenylamino)-4-fluoro-benzothiazol-6-carboxylic acid hydroxyamide; 7-(4-Iodo-2-methyl-phenylamino)-4-nitro-benzooxazole-6-carboxylic acid hydroxyamide; 4-Fluoro-5-(4-iodo-2-methyl-phenylamino)-benzothiazole-6-carboxylic acid cyclopropylmethoxy-amide; 4-Fluoro-5-(4-iodo-2-methyl-phenylamino)-benzooxazole-6-carboxylic acid cyclopropylmethoxy-amide; 5-(2-Chloro-4-iodo-phenylamino)-6,7-difluoro-3H-benzoimidazole-4-carboxylic acid cyclopropylmethoxy-amide; 6,7-Difluoro-2-(2-hydroxy-ethyl)-5-(4-iodo-2-methyl-phenylamino)-3H-benzoimidazole-4-carboxylic acid cyclopropylmethoxy-amide; 6,7-Difluoro-5-(4-iodo-2-methyl-phenylamino)-benzooxazole-4-carboxylic acid cyclopropylmethoxy-amide; 6,7-Difluoro-5-(4-iodo-2-methyl-phenylamino)-benzothiazole-4-carboxylic acid cyclopropylmethoxy-amide; 7,8-Difluoro-6-(4-iodo-2-methyl-phenylamino)-quinoxaline-5-carboxylic acid cyclopropylmethoxy-amide; 6-(4-Iodo-2-methyl-phenylamino)-8-nitro-quinoxaline-5-carboxylic acid cyclopropylmethoxy-amide; 5-(4-Iodo-2-methyl-phenylamino)-8-nitro-quinoxaline-6-carboxylic acid cyclopropylmethoxy-amide; 8-Chloro-5-(4-iodo-2-methyl-phenylamino)-quinoxaline-6-carboxylic acid cyclopropylmethoxy-amide; 3-Cyclopropyl-7-(4-iodo-2-methyl-phenylamino)-3H-benzoimidazole-4,6-dicarboxylic acid 4-dimethylamide 6-cyclopropylmethoxy-amide; 7-Bromo-4-(4-iodo-2-methyl-phenylamino)-benzooxazole-5-carboxylic acid cyclopropylmethoxy-amide; 7-(2-Chloro-4-iodo-phenylamino)-4-fluoro-benzothiazole-6-carboxylic acid cyclopropylmethoxy-amide; and 7-(4-Iodo-2-methyl-phenylamino)4-nitro-benzooxazole-6-carboxylic acid cyclopropylmethoxy-amide.

C. SYNTHESIS

The disclosed compounds can be synthesized according to the following eleven Schemes, or variants thereof. These synthetic strategies are further exemplified in Examples 1–22 below.

Scheme 1

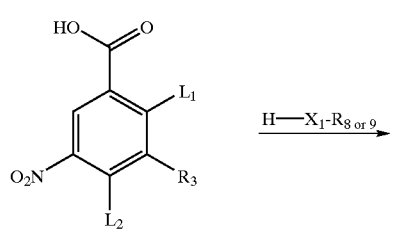

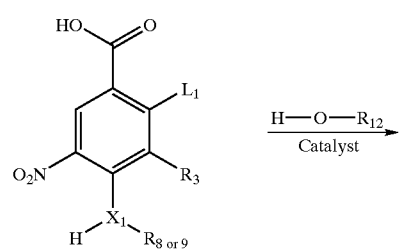

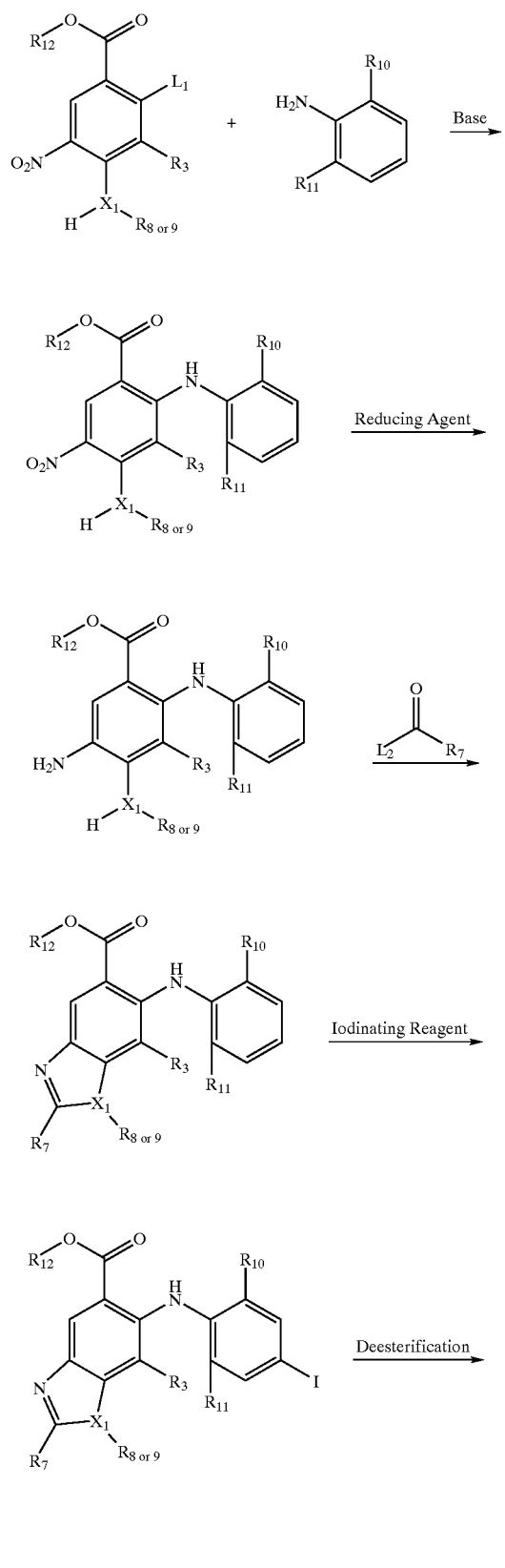

-continued
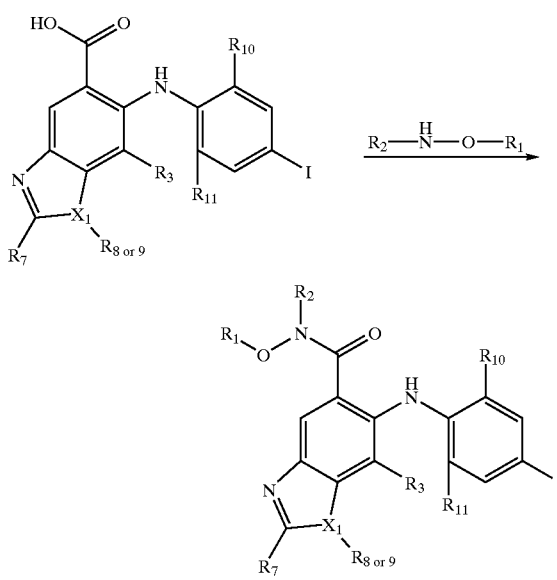
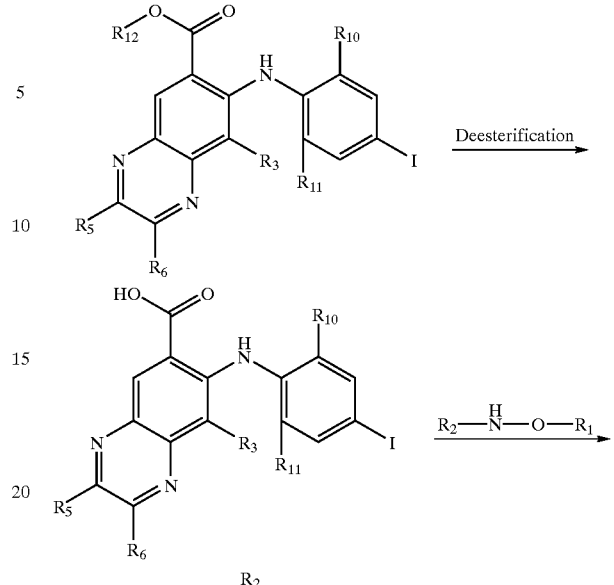
Scheme 2
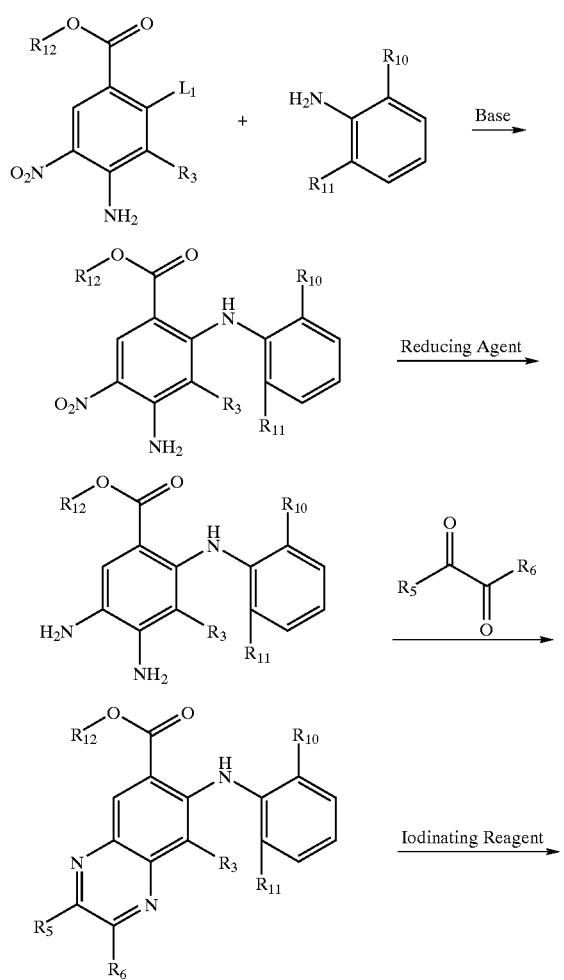
Scheme 3
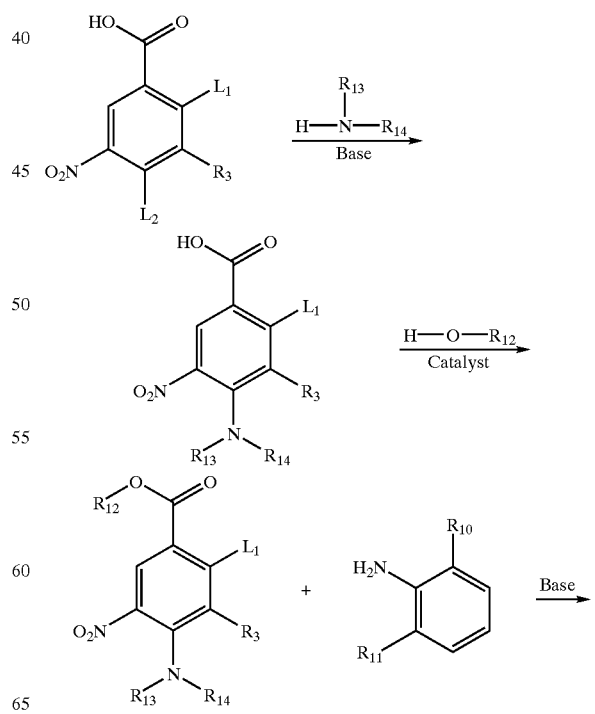

13
-continued
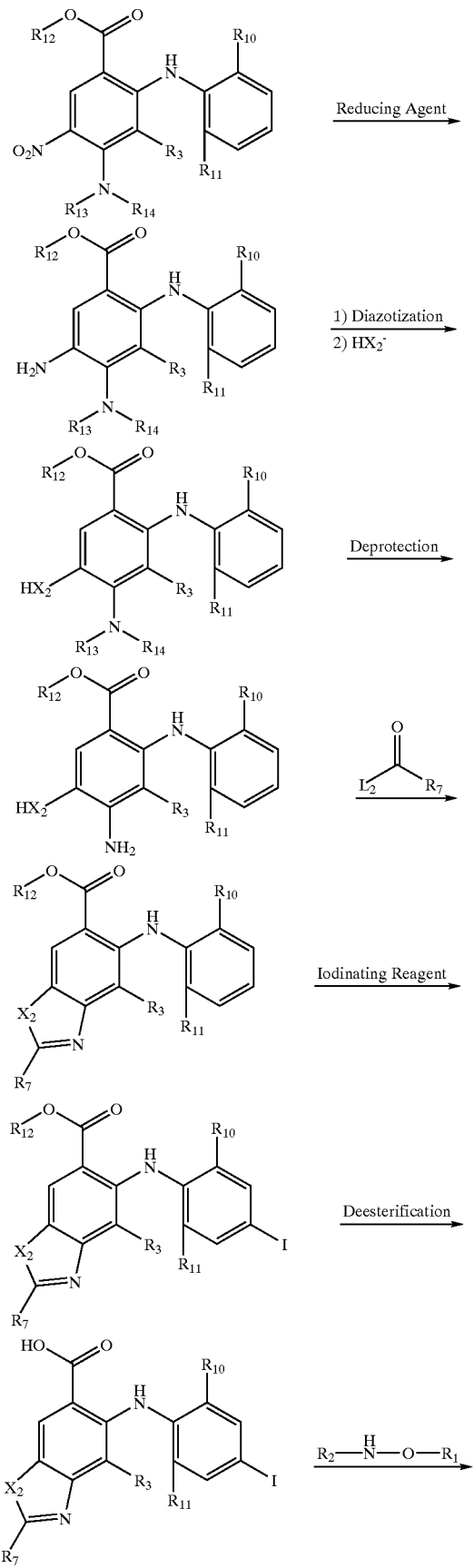
14
-continued
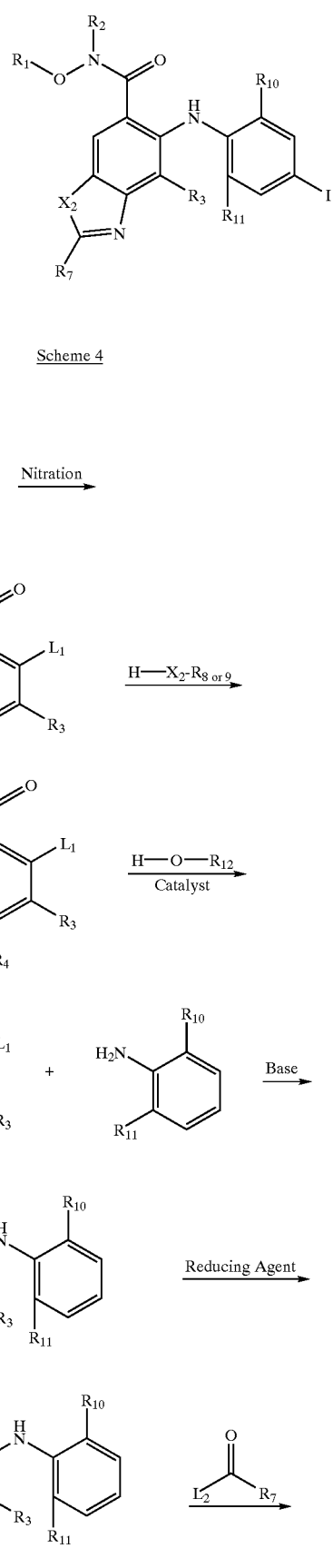
Scheme 4

15
-continued
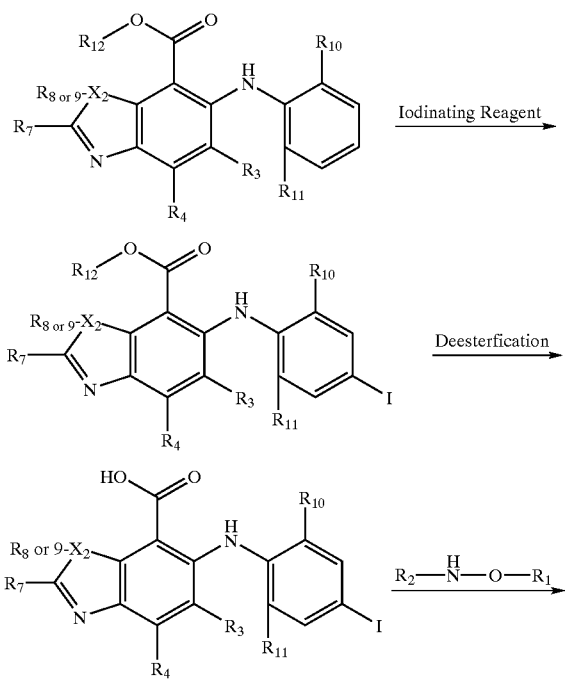
Scheme 5
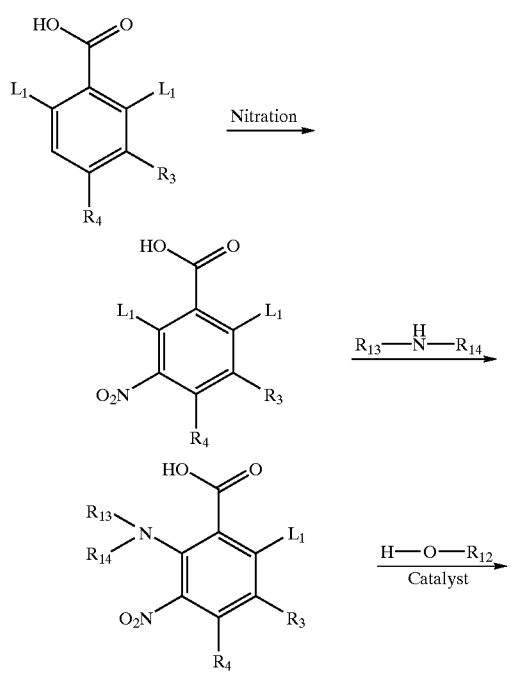
16
-continued
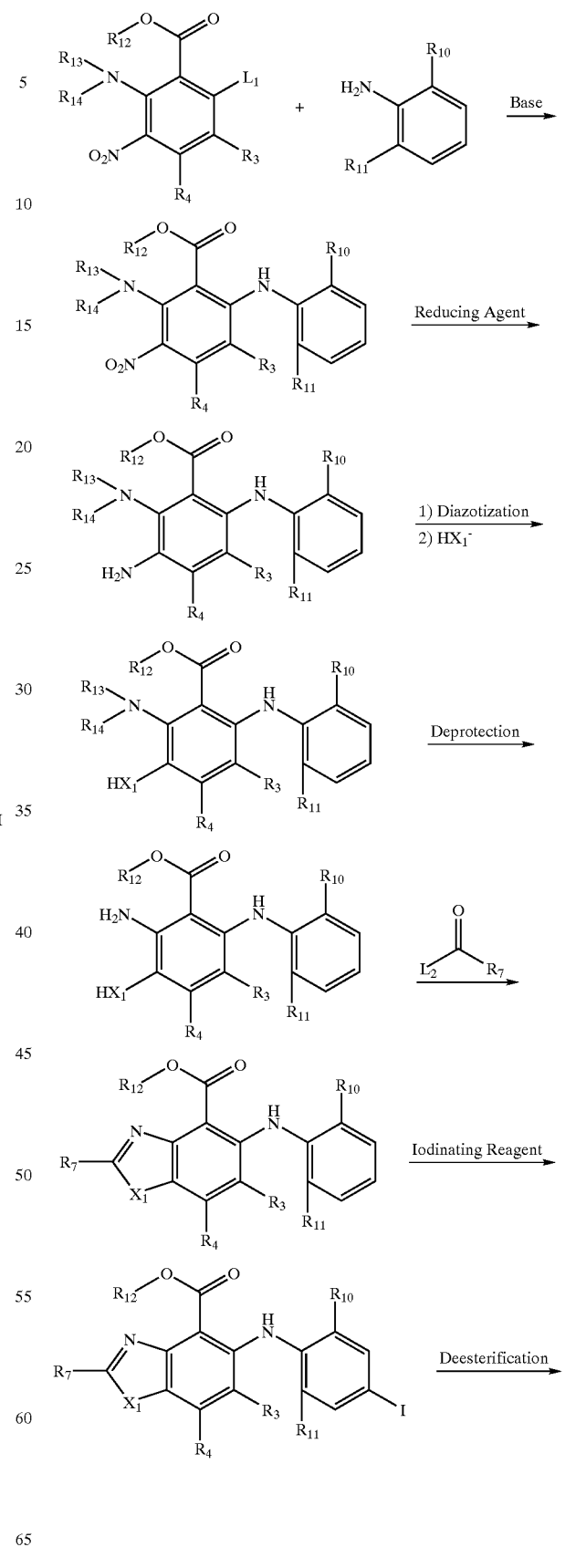

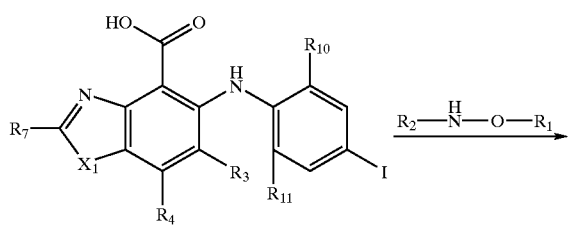
Scheme 6
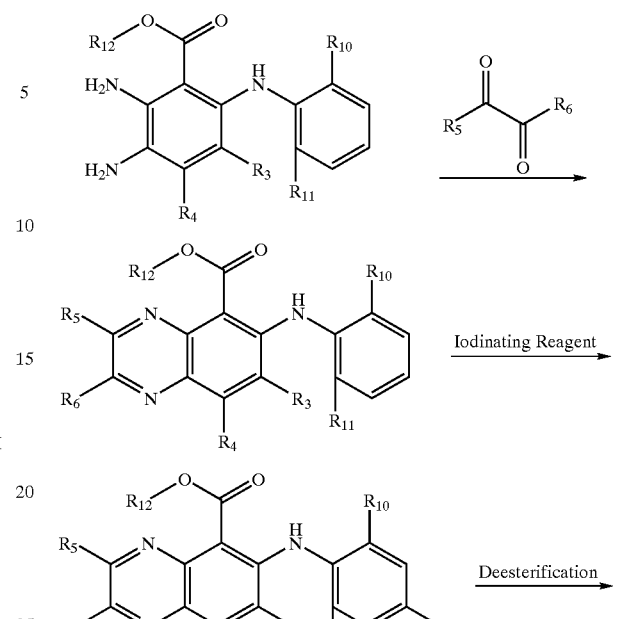
Scheme 7
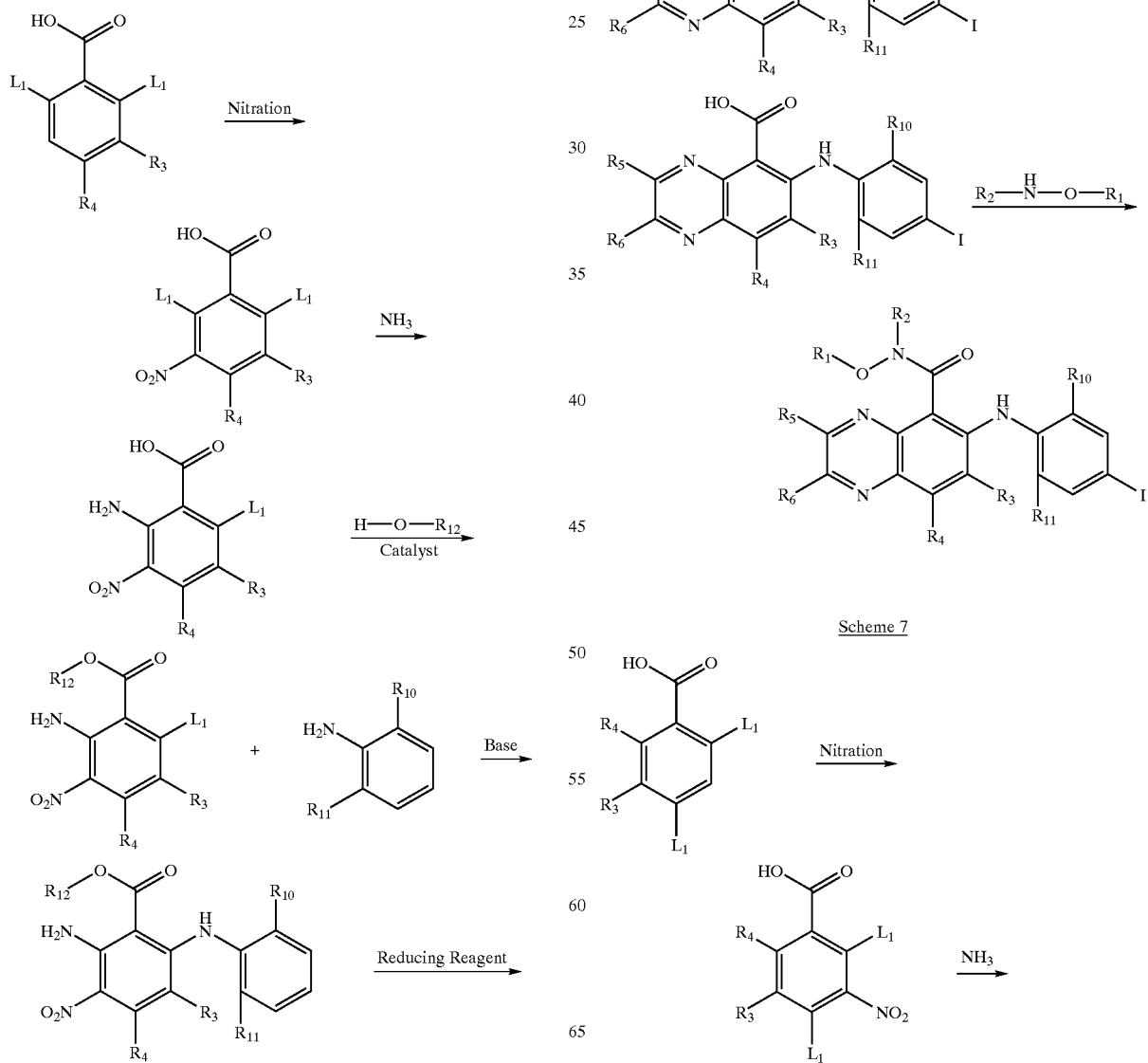

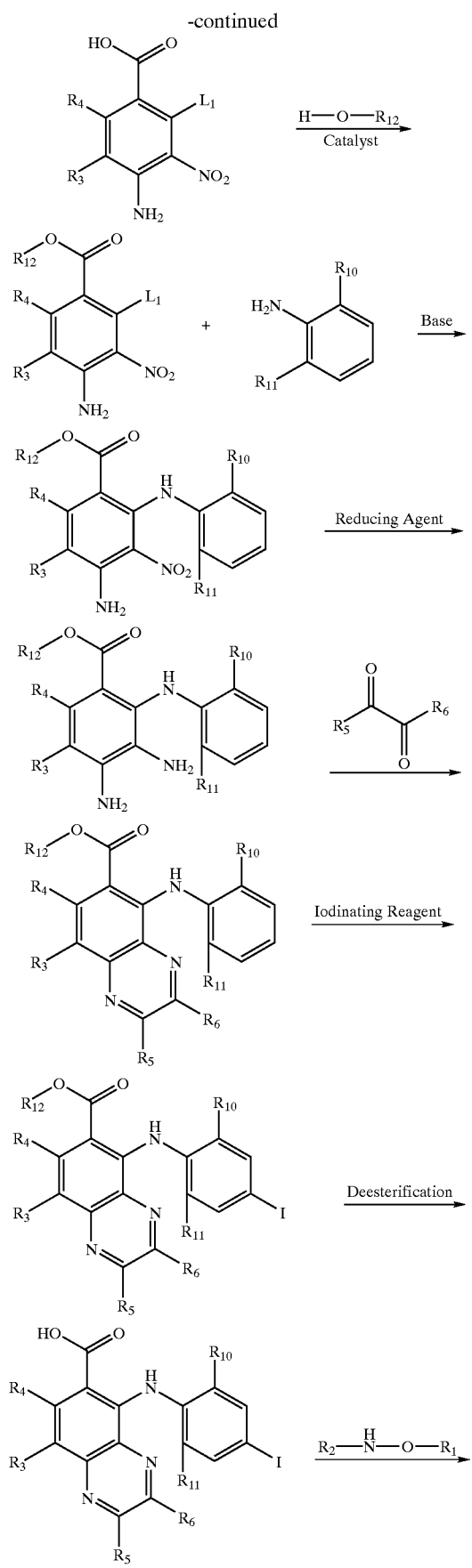
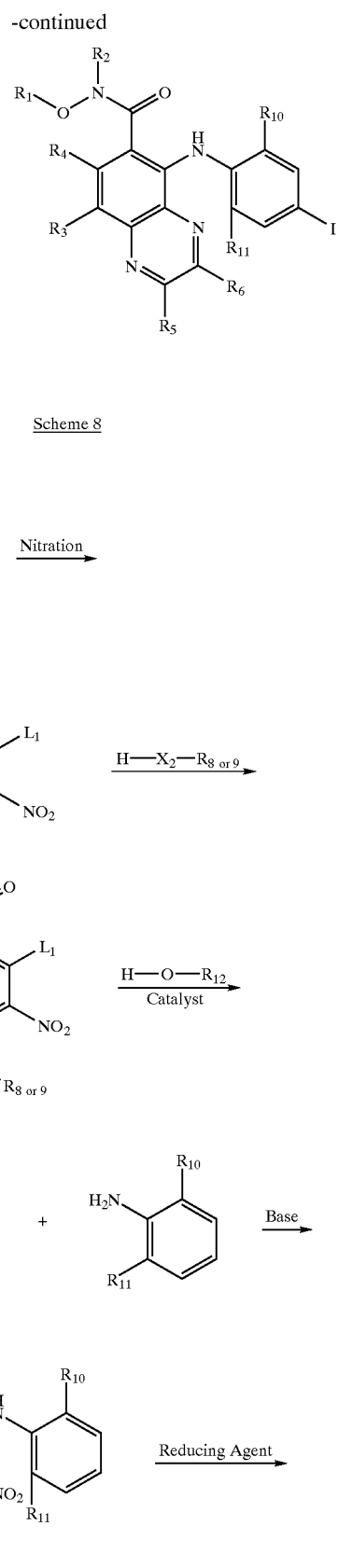
Scheme 8

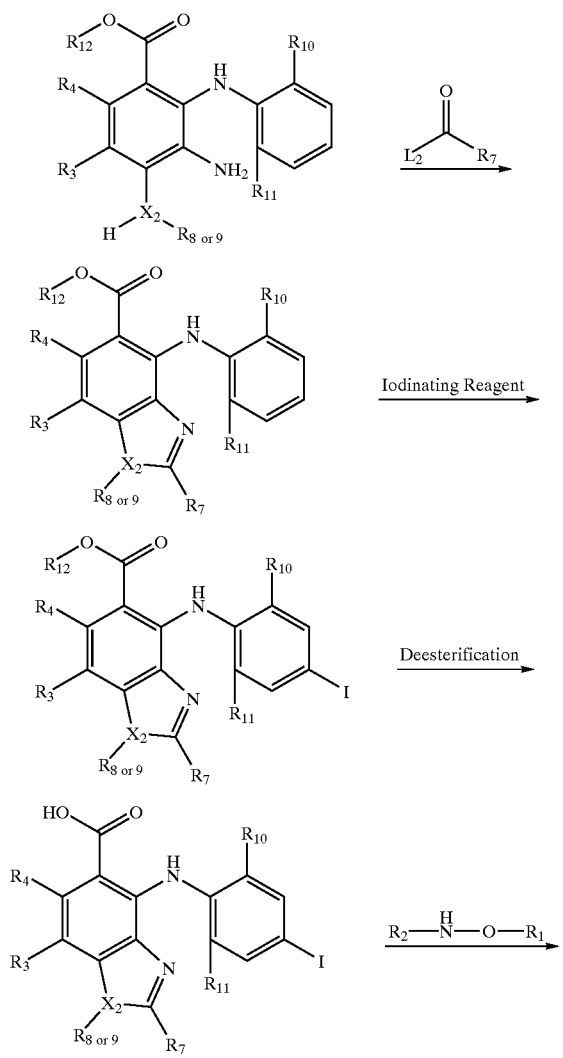
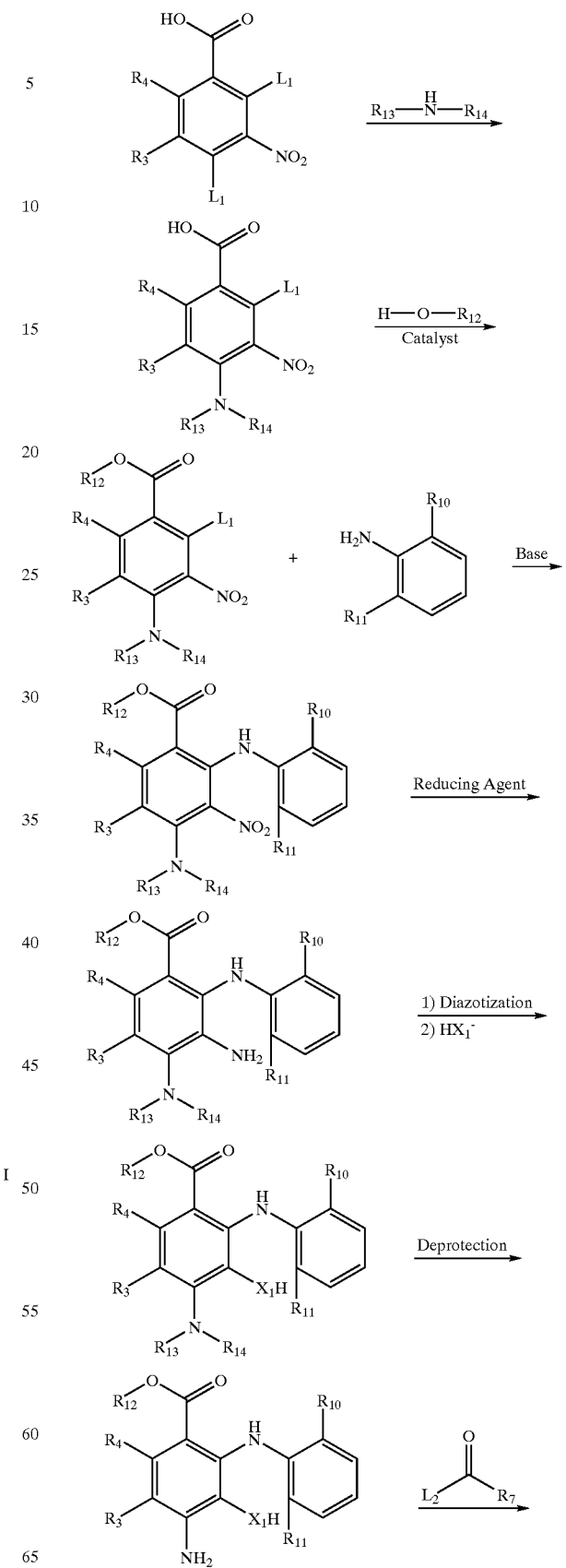
Scheme 9
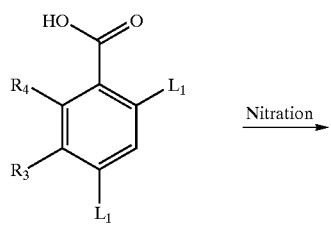

23
-continued
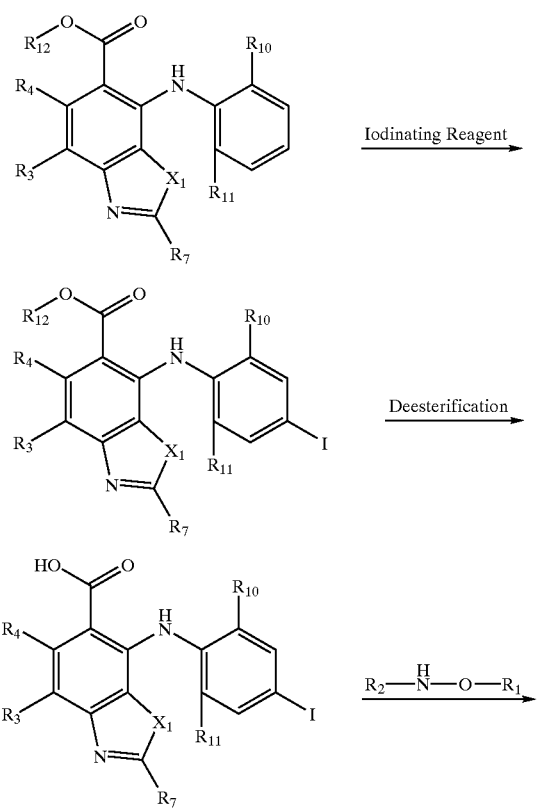
Scheme 10
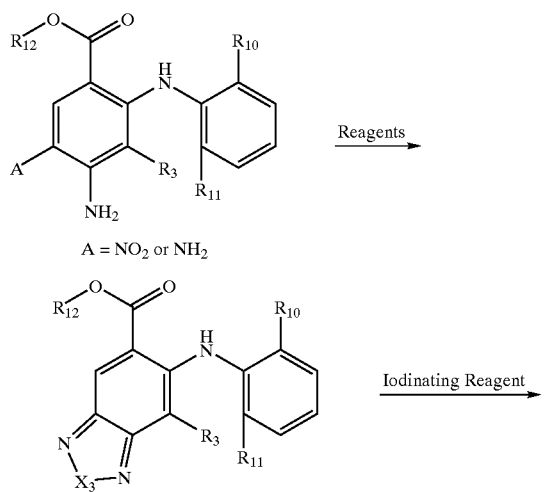
24
-continued
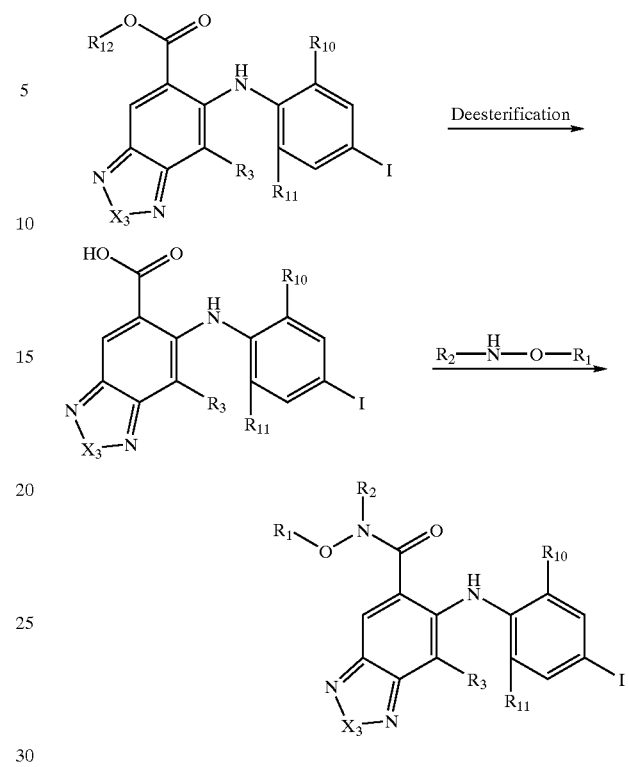
Scheme 11
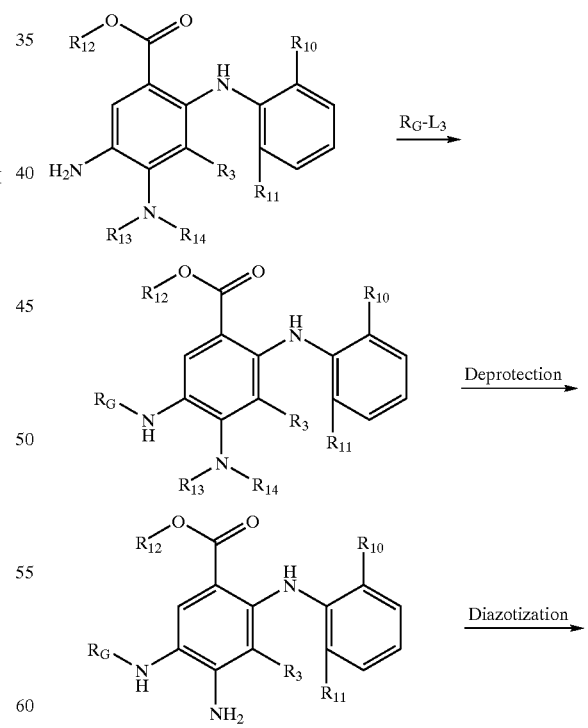

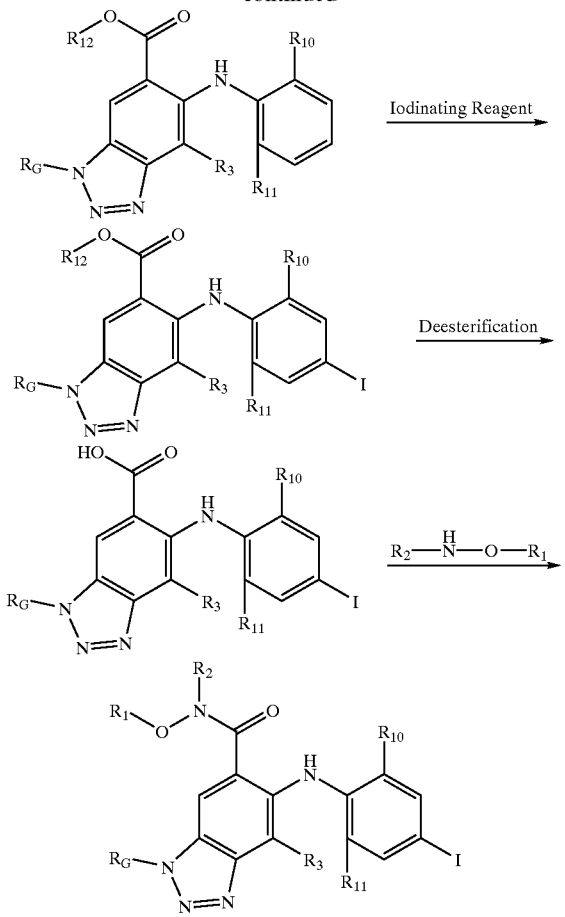

D. USES

The disclosed compositions are useful as both prophylactic and therapeutic treatments for diseases or conditions as provided in the Summary section, as well as diseases or conditions modulated by the MEK cascade. Examples include stroke, heart failure, osteoarthritis, rheumatoid arthritis, organ transplant rejection, and a variety of tumors such as ovarian, lung, pancreatic, brain, prostatic, and colon.

1. Dosages

Those skilled in the art will be able to determine, according to known methods, the appropriate dosage for a patient, taking into account factors such as age, weight, general health, the symptoms requiring treatment, and the presence of other medications. In general, an effective amount will be between 0.1 and 1000 mg/kg per day, preferably between 1 and 300 mg/kg body weight, and daily dosages will be between 10 and 5000 mg for an adult subject of normal weight. Capsules, tablets or other formulations (such as liquids and film-coated tablets) may be of between 5 and 200 mg, such as 10, 15, 25, 35, 50 mg, 60 mg, and 100 mg can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Related Compounds

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$ alkyl, cycloalkyl, aryl, heteroaryl, or non-aromatic heterocyclic), amino acid addition salts, esters, and amides which are within a reasonable benefit/risk ratio, pharmacologically effective, and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See, for example, S. M. Berge, et al., "Pharmaceutical Salts," *J. Pharm. Sci.,* 1977, 66:1–19 which is incorporated herein by reference. Representative pharmaceutically acceptable amides of the invention include those derived from ammonia, primary $C_{1-6}$ alkyl amines and secondary di($C_{1-6}$ alkyl)amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

The invention also includes disclosed compounds having one or more functional groups (e.g., hydroxyl, amino, or carboxyl) masked by a protecting group. Some of these masked or protected compounds are pharmaceutically acceptable; others will be useful as intermediates. Synthetic intermediates and processes disclosed herein, and minor modifications thereof, are also within the scope of the invention. Examples of synthetic intermediates of the invention include PD 202885, PD 203337, PD 218001, PD 254551, and PD 201601.

Hydroxyl Protecting Groups

Hydroxyl protecting groups include: ethers, esters, and protection for 1,2- and 1,3-diols. The ether protecting groups include: methyl, substituted methyl ethers, substituted ethyl ethers, substituted benzyl ethers, silyl ethers and conversion of silyl ethers to other functional groups.

Substituted Methyl Ethers

Substituted methyl ethers include: methoxymethyl, methylthiomethyl, t-utylthiomethyl, (phenyldimethylsilyl) methoxymethyl, benzyloxymethyl, p-ethoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloro-ethoxy)methyl, 2-(trimethylsilyl)ethoxymethyl, tetrahydropyranyl, 3-bromotetrahydro-pyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro4-methyl)phenyl]-4-methoxypiperidin-4-yl, 1,4-dioxan-2-yl, tetrahydrofuranyl, tetrahydrothiofuranyl, and 2,3,3a,4,5,6,7,7a-octahydro-7,8,8-trimethyl-4,7-ethanobenzofuran-2-yl.

Substituted Ethyl Ethers

Substituted ethyl ethers include: 1-ethoxyethyl, 1-(2, chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilyethyl, 2-(phenylselenyl)ethyl, t-butyl, allyl, p-chlorophenyl, p-methoxyphenyl, 2,4-dinitrophenyl, and benzyl.

Substituted Benzyl Ethers

Substituted benzyl ethers include: p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyl-diphenylmethyl, p-methoxyphenyldiphenylmethyl, di(p-methoxyphenyl)phenylmethyl, tri-(p-methoxyphenyl) methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"tris (benzoyloxyphenyl)methyl, 3-(imidazol-1-ylmethyl)bis(4', 4"-dimethoxyphenyl)-methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Silyl ethers include: trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxy-phenylsilyl.

Esters

Esters protecting groups include: esters, carbonates, assisted cleavage, miscellaneous esters, and sulfonates.

Esters

Examples of protective esters include: formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, and 2,4,6-trimethylbenzoate(mesitoate).

Carbonates

Carbonates include: methyl, 9-fluorenylmethyl, ethyl, 2,2, 2-trichloroethyl, 2-(trimethylsilyl)ethyl, 2-(phenylsulfonyl) ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage protecting groups include: 2-iodobenzoate, 4-azido-butyrate, 4-nitro-4-methylpentanoate, o-(dibromomethyl)benzoate, 2-formylbenzene-sulfonate, 2-(methylthiomethoxy)ethyl carbonate, 4-(methylthiomethoxymethyl)benzoate, and 2-(methylthiomethoxymethyl)benzoate.

Miscellaneous Esters

In addition to the above classes, miscellaneous esters include: 2,6-dichloro-4-methylphenoxyacetate, 2,6-dichloro-4-(1,1,3,3-tetramethylbutyl) phenoxyacetate, 2,4-bis(1,1-dimethylpropyl) phenoxyacetate, chlorodiphenylacetate, isobutyrate, monosuccinoate, (E)-2-methyl-2-butenoate (tigloate), o-(methoxycarbonyl) benzoate, p-P-benzoate, α-naphthoate, nitrate, alkyl N,N,N', N'-tetramethyl-phosphorodiamidate, N-phenylcarbamate, borate, dimethylphosphinothioyl, and 2,4-dinitrophenylsulfenate.

Sulfonates

Protective sulfates includes: sulfate, methanesulfonate (mesylate), benzylsulfonate, and tosylate.

Protection for 1,2- and 1,3-DIOLS

The protection for 1,2 and 1,3-diols group includes: cyclic acetals and ketals, cyclic ortho esters, and silyl derivatives.

Cyclic Acetals and Ketals

Cyclic acetals and ketals include: methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Cyclic ortho esters include: methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Protection for the Carboxyl Group

Esters

Ester protecting groups include: esters, substituted methyl esters, 2-substituted ethyl esters, substituted benzyl esters, silyl esters, activated esters, miscellaneous derivatives, and stannyl esters.

Substituted Methyl Esters

Substituted methyl esters include: 9-fluorenylmethyl, methoxymethyl, methylthiomethyl, tetrahydropyranyl, tetrahydrofuranyl, methoxyethoxymethyl, 2-(trimethylsilyl) ethoxy-methyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

2-Substituted ethyl esters include: 2,2,2-trichloroethyl, 2-haloethyl, |-chloroalkyl, 2-(trimethylsily)ethyl, 2-methylthioethyl, 1,3-dithianyl-2-methyl, 2(p-nitrophenyl-sulfenyl)-ethyl, 2-(p-toluenesulfonyl)ethyl, 2-(2'-pyridyl) ethyl, 2-(diphenyl-phosphino)ethyl, 1-methyl-1-phenylethyl, t-butyl, cyclopentyl, cyclohexyl, allyl, 3-buten-1-yl, 4-(trimethylsily)-2-buten-1-yl, cinnamyl, α-methylcinnamyl, phenyl, p-(methylmercapto)-phenyl, and benzyl.

Substituted Benzyl Esters

Substituted benzyl esters include: triphenylmethyl, diphenylmethyl, bis(o-nitrophenyl)methyl, 9-anthrylmethyl, 2-(9,10-dioxo)anthrylmethyl, 5-dibenzo-suberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, and 4-P-benzyl.

Silyl Esters

Silyl esters include: trimethylsilyl, triethylsilyl, t-butyldimethylsilyl, i-propyidimethylsilyl, phenyldimethylsilyl, and di-t-butylmethylsilyl.

Miscellaneous Derivatives

Miscellaneous derivatives includes: oxazoles, 2-alkyl-1,3-oxazolines, 4-alkyl-5-oxo-1,3-oxazolidines, 5-alkyl4-oxo-1,3-dioxolanes, ortho esters, phenyl group, and pentaaminocobalt(II) complex.

Stannyl Esters

Examples of stannyl esters include: triethylstannyl and tri-n-butylstannyl.

Amides and Hydrazides

Amides include: N,N-dimethyl, pyrrolidinyl, piperidinyl, 5,6-dihydrophenanthridinyl, o-nitroanilides, N-7-nitroindolyl, N-8-nitro-1,2,3,4-tetrahydroquinolyl, and p-P-benzenesulfonamides. Hydrazides include: N-phenyl, N,N'-diisopropyl and other dialkyl hydrazides.

Protection for the Amino Group

Carbamates

Carbamates include: carbamates, substituted ethyl, assisted cleavage, photolytic cleavage, urea-type derivatives, and miscellaneous carbamates.

Carbamates

Carbamates include: methyl and ethyl, 9-fluorenylmethyl, 9-(2-sulfo)fluorenylmethyl, 9-(2,7-dibromo) fluorenylmethyl, 2,7-di-t-butyl-[9-(10,10-dioxo-10,10,10,10-tetrahydro-thioxanthyl)]methyl, and 4-methoxyphenacyl.

Substituted Ethyl

Substituted ethyl protective groups include: 2,2,2-trichloroethyl, 2-trimethylsilylethyl, 2-phenylethyl, 1-(1-adamantyl)-1-methylethyl, 1,1-dimethyl-2-haloethyl, 1,1dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'-and 4'-pyridyl)ethyl, 2-(N,N-icyclohexylcarboxamido)-ethyl, t-butyl, 1-adamantyl, vinyl, allyl, 1-isopropylallyl, connamyl, 4-nitrocinnamyl, quinolyl, N-hydroxypiperidinyl, alkyldithio, benzyl, p-methoxybenzyl, p-nitrobenzyl, p-bromobenzyl, p-chloro-benzyl, 2,4-dichlorobenzyl, 4-methylsulfinylbenzyl, 9-anthrylmethyl, and diphenylmethyl.

Assisted Cleavage

Protection via assisted cleavage includes: 2-methylthioethyl, 2-methylsulfonyl-ethyl, 2-(p-toluenesulfonyl)ethyl, [2-(1,3-dithianyl)]methyl, 4-methylthiophenyl, 2,4-dimethyl-thiophenyl, 2-phosphonioethyl, 2-triphenyl-phosphonioisopropyl, 1,1-dimethyl-2-cyanoethyl, m-chloro-p-acyloxybenzyl, p-(dihydroxyboryl)benzyl, 5-benzisoxazolyimethyl, and 2-(trifluoromethyl)-6-chromonylmethyl.

Photolytic Cleavage

Photolytic cleavage methods use groups such as: m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of of urea-type derivatives include: phenothiazinyl-(10)-carbonyl derivative, N'-p-toluenesulfonylaminocarbonyl, and N'-phenylaminothiocarbonyl.

Miscellaneous Carbamates

In addition to the above, miscellaneous carbamates include: t-amyl, S-benzyl thiocarbamate, p-cyanobenzyl, cyclobutyl, cyclohexyl, cyclopentyl, cyclopropylmethyl, p-decyloxy-benzyl, diisopropylmethyl, 2,2-dimethoxy-carbonylvinyl, o-(N,N-dimethyl-carboxamido)-benzyl, 1,1-dimethyl-3(N,N-dimethylcarboxamido)propyl, 1,1-dimethyl-propynyl, di(2-pyridyl)methyl, 2-furanylmethyl, 2-iodoethyl, isobornyl, isobutyl, isonicotinyl, p(p'-methoxyphenyl-azo)benzyl, 1-methylcyclobutyl, 1-methylcyclohexyl, 1-methyl-1-cyclopropylmethyl, 1-methyl-(3,5-dimethoxyphenyl)ethyl, 1-methyl-1(p-henylazophenyl)-ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)-benzyl, and 2,4,6-trimethylbenzyl.

Amides

Amides

Amides includes: N-formyl, N-acetyl, N-chloroacetyl, N-trichloroacetyl, N-trifluoroacetyl, N-phenylacetyl, N-3-phenylpropionyl, N-picolinoyl, N-3-pyridyl-carboxamide, N-benzoylphenylalanyl derivative, N-benzoyl, and N-p-phenylbenzoyl.

Assisted Cleavage

Assisted cleavage groups include: N-o-nitrophenylacetyl, N-o-nitrophenoxyacetyl, N-acetoacetyl, (N'-dithiobenzyloxycarbonylamino)acetyl, N-3-(p-hydroxphenyl)propionyl, N-3-(o-nitrophenyl)propionyl, N-2-methyl-2-(o-nitrophenoxy)propionyl, N-2-methyl-2-(o-phenylazophenoxy)propionyl, N4-chlorobutyryl, N-3-methyl-3-nitrobutyryl, N-onitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

Cyclic imide derivatives include: N-phthalimide, N-dithiasuccinoyl, N-2,3-diphenyl-maleoyl, N-2,5-dimethylpyrrolyl, N-1,1,4,4-tetramethyl-disilylazacyclopentane adduct, 5-substituted 1,3-dimethyl-1,3,5-triazacyclohexan-2one, 5-substituted 1,3-dibenzyl-1,3,5-triazacyclohexan-2-one, and 1-substituted 3,5-dinitro-4-pyridonyl.

Special—NH Protective Groups

Protective groups for—NH include: N-alkyl and N-aryl amines, imine derivatives, enamine derivatives, and N-hetero atom derivatives (such as N-metal, N—N, N—P, N—Si, and N—S), N-sulfenyl, and N-sulfonyl.

N-Alkyl and N-Aryl Amines

N-alkyl and N-aryl amines include: N-methyl, N-allyl, N-[2-(trimethylsilyl)ethoxyl]-methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

Imine derivatives include: N-1,1-dimethylthiomethylene, N-benzylidene, N-p-methoxybenzylidene, N-diphenylmethylene, N-[(2-pyridyl)mesityl]methylene, N-(N',N'-dimethylaminomethylene), N,N'-isopropylidene, N-p-nitrobenzylidene, N-salicylidene, N-5-chlorosalicylidene, N-(5-chloro-2-hydroxyphenyl)-phenylmethylene, and N-cyclohexylidene.

Enamine Derivative

An example of an enamine derivative is N-(5,5-dimethyl-3-oxo-1-cyclohexenyl).

N-Hetero Atom Derivatives

N-metal derivatives include: N-borane derivatives, N-diphenylborinic acid derivative, N-[phenyl(pentacarbonylchromium- or -tungsten)]carbenyl, and N-copper or N-zinc chelate. Examples of N—N derivatives include: N-nitro, N-nitroso, and N-oxide. Examples of N—P derivatives include: N-diphenylphosphinyl, N-dimethylthiophosphinyl, N-diphenylthiophosphinyl, N-dialkyl phosphoryl, N-dibenzyl phosphoryl, and N-diphenyl phosphoryl. Examples of N-sulfenyl derivatives include: N-benzenesulfenyl, N-o-nitrobenzenesulfenyl, N-2,4-dinitrobenzenesulfenyl, N-pentachlorobenzene-sulfenyl, N-2-nitro-4-methoxy-benzenesulfenyl, N-triphenylmethylsulfenyl, and N-3-nitropyridinesulfenyl. N-sulfonyl derivatives include: N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxy-benzenesulfonyl, N-pentamethylbenzenesulfonyl, N-2,3,5,6-tetramethyl-4-methoxybenzene-sulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethyl-chroman-6-sulfonyl, N-methanesulfonyl, N-β-trimethylsilylethanesulfonyl, N-9-anthracenesulfonyl, N4-(4',8'-dimethoxynaphthylmethyl)-benzenesulfonyl, N-benzylsulfonyl, N-trifluoromethylsulfonyl, and N-phenacylsulfonyl.

Disclosed compounds which are masked or protected may be prodrugs, compounds metabolized or otherwise transformed in vivo to yield a disclosed compound, e.g., transiently during metabolism. This transformation may be a hydrolysis or oxidation which results from contact with a bodily fluid such as blood, or the action of acids, or liver, gastrointestinal, or other enzymes.

Features of the invention are further described in the examples below.

E. EXAMPLES

Example 1

Preparation of 7-fluoro-6-(4-iodo-2-methyl-phenylamino)-1H-benzoimidazole-5-carboxylic acid (PD 205293) (APK $IC_{50}$=14 nM; colon 26 cells, $IC_{50}$=>10 micromolar)

Step a: Preparation of 5-nitro-2,3,4-trifluorobenzoic acid

To gently stirring concentratedsulfuric acid (50 ml) was added fuming nitric acid (3.4 ml, 0.076 mol). Solid 2,3,4-trifluorobenzoic acid (10.00 g, 0.05565 mol) was added directly in increments. After stirring 45 minutes, the reaction mixture had become an orange homogeneous solution which was then poured over chilled water (400 ml). The resulting aqueous suspension was extracted with diethyl ether (3×200 ml). The combined extracts were dried with anhydrous magnesium sulfate and concentrated in vacuo to yield 12.30 g of a dull, light-yellow solid. Recrystallization from chloroform (50 ml) afforded 9.54 g of the pale yellow microcrystalline product; 78% yield; m.p. ; $^1$H-NMR (400 MHz; DMSO)δ 14.29 (broad s, 1H), 8.43–8.38 (m, 1H); $^{13}$C-NMR (100 MHz; DMSO) δ162.41, 154.24 (dd, $J_{C-F}$=270.1, 10.7 Hz), 148.35 (dd, $J_{C-F}$=267.0, 9.2 Hz), 141.23 (dt, $J_{C-F}$=253.4 Hz), 133.95,1 23.30 (d, $J_{C-F}$=2.2 Hz), 116.92 (dd, $J_{C-F}$=18.2, 3.8 Hz); $^{19}$F-NMR (376 MHz; DMSO) δ–120.50 to –120.63 (m), –131.133 to –131.27 (m), –153.63 to –153.74 (m).

Step b: Preparation of 4-amino-2,3-difluoro-5-nitrobenzoic acid

Solid 5-nitro-2,3,4-trifluorobenzoic acid (0.75 g, 0.00339 mol) was dissolved in concentrated ammonium hydroxide (25 ml) to give instantly a yellow solution. A precipitate began to form within five minutes, after which time the mixture was acidified to pH 0 with concentrated aqueous hydrochloric acid. A yellow precipitate rapidly formed. The mixture was heated to boiling and was filtered hot. The yellow solids were washed with 10% aqueous hydrochloric acid and were suction dried to afford 0.47 g of a yellow powder; 64% yield; $^1$H-NMR (400 MHz; DMSO) δ13.32 (s, 1H), 8.36 (d, 1H, J=7.6 Hz), 7.98 (s, 2H); $^{19}$F-NMR (376 MHz; DMSO) δ–128.69 to –128.76 (m), –153.60 (d).

Step c: Preparation of methyl 4-amino-2,3-difluoro-5-nitrobenzoate

Hydrogen chloride gas was dissolved in anhydrous methanol (30 ml) until the solution was warm. The solid 4-amino-2,3-difluoro-5-nitrobenzoic acid (0.47 g; 0.00215 mol) was dissolved in this solution and the reaction mixture was brought to reflux with vigorous stirring for 23 hours under a nitrogen atmosphere. The reaction mixture was allowed to cool slowly on the bench. A yellow precipitate formed and was collected by vacuum filtration and dried with suction to afford 0.35 g of yellow microfilaments; 70% yield; m.p. 183.5–184° C.; $^1$H-NMR (400 MHz; DMSO) δ8.36 (dd, 1H, J=7.3, 1.7 Hz), 8.06 (s, 2H), 3.78 (s, 3H); $^{19}$F-NMR (376 MHz; DMSO) δ–128.85 to –128.92 (m), –153.29 (d); MS (APCl–) 231 (M–1, 100); IR (KBr) 3433, 3322, 1700, 1650, 1549, 1343, 1285 cm$^{-1}$; Anal. calcd/found for: $C_8H_6F_2N_2O_4$ C, 41.39/41.40; H, 2.61/2.50; N, 12.07/11.98; F, 16.37/16.58.

Step d: Preparation of methyl 4-amino-3-fluoro-2-(2-methyl-phenylamino)-5-nitrobenzoate The solid methyl 4-amino-2,3-difluoro-5-nitrobenzoate (0.087 g, 3.7×10$^{-4}$ mol) was dissolved in ortho-toluidine (3 ml, 0.028 mol). The reaction mixture was stirred at 200° C. for 35 minutes under a nitrogen atmosphere. The mixture was then partitioned between diethyl ether (150 ml) and 10% aqueous hydrochloric acid (150 ml). The ether phase was dried with anhydrous magnesium sulfate and was concentrated in vacuo to a crude solid. The crude product was dissolved in 5 ml of dichloromethane and was filtered through a flash silica plug. Elution with dichloromethane afforded 0.0953 g of a yellow solid; 81% yield; m.p. 164–168° C.; $^1$H-NMR (400 MHz; DMSO) δ9.20 (s, 1H), 8.52 (d, 1H, J=1.7 Hz), 7.57 (s, 2H), 7.19 (d, 1H, J=7.3 Hz), 7.12–7.08 (m, 1H), 7.02–6.98 (m, 1H), 6.95–6.91 (m, 1H), 3.78 (s, 3H), 2.21 (s, 3H); $^{19}$F-NMR (376 MHz; DMSO) δ–141.13 (s); MS (APCl+) 320 (M+1, 100); (APCl–) 318 (M–1, 100); IR (KBr) 3467, 3346, 1690, 1305 cm$^{-1}$; Anal.

calcd/found for: $C_{15}H_{14}FN_3O_4$.0.21 $H_2O$ C, 55.77/55.97; H, 4.50/4.55; N, 13.01/12.61; F, 5.88/5.95.

Step e: Preparation of methyl 4,5-diamino-3-fluoro-2-(2-methyl-phenylamino)benzoate To a mixture comprised of methyl 4-amino-3-fluoro-2-(2-methyl-phenylamino)-5-nitrobenzoate (2.52 g, 0.00789 mol), tetrahydrofuran (50 ml), methanol (50 ml) and washed Raney nickel (0.5 g) was initially applied 48.6 psi of hydrogen gas at 30.2° C. in a shaker for 4 hours 48 minutes. The mixture was filtered and the filtrate concentrated in vacuo to afford 2.20 g of a salmon-colored amorphous solid; 96% yield; $^1$H-NMR (400 MHz; DMSO) δ7.84 (s, 1H), 7.04 (d, 1H, J=7.1 Hz), 6.98 (d, 1H, J=1.2 Hz), 6.95–6.91 (m, 1H), 6.68–6.64 (m, 1H), 6.40–6.36 (m, 1H), 5.39 (s, 2H), 4.73 (s, 2H), 3.66 (s, 3H), 2.21 (s, 3H); $^{19}$F-NMR (376 MHz; DMSO) δ–139.66 (s).

Step f: Preparation of methyl 7-fluoro-6-(2-methyl-phenylamino)-1H-benzoimidazole-5-carboxylate A stirring solution comprised of methyl 4,5-diamino-3-fluoro-2-(2-methyl-phenylamino)-benzoate (1.78 g, 0.00615 mol) in formic acid (Aldrich, 95–97%, 100 ml, 2.5 mol) was brought to reflux for 3 hours followed by concentration in vacuo to give a crude brown solid. The crude product was triturated with chloroform (40 ml) and subsequently collected by vacuum filtration. The solids were dried with suction to afford 1.09 g of a light-lavender powder. The filtrate was concentrated in vacuo to a crude solid which was triturated with 10 ml of chloroform-dichloromethane. These solids were collected by vacuum filtration, rinsed with dichloromethane, and were suction-dried to give an additional 0.55 g of a light-lavender powder (total yield: 1.64 g); 87% yield; m.p. 259–262° C.; $^1$H-NMR (400 MHz; DMSO) δ8.42 (s, 1H), 8.03 (s, 1H), 7.93 (broad s, 1H), 7.12 (d, 1H, J=7.0 Hz), 6.99–6.95 (m, 1H), 6.75–6.71 (m, 1H), 6.48–6.44 (m, 1H), 3.81 (s, 3H), 2.30 (s, 3H); $^{19}$F-NMR (376 MHz; DMSO) δ–132.84 (s); MS (APCl+) 300 (M+1, 100); (APCl–) 298 (M–1, 100); IR (KBr) 3322, 1689, 1437, 1326, 1218 cm$^{-1}$; Anal. calcd/found for: $C_{16}H_{14}FN_3O_2$.0.32 $H_2O$ C, 62.99/63.01; H, 4.84/4.61; N, 13.77/13.70.

Step g: Preparation of methyl 7-fluoro-6-(4-iodo-2-methyl-phenylamino)-1H-benzoimidazole-5-carboxylate A stirring mixture comprised of methyl 7-fluoro-6-(2-methyl-phenylamino)-1H-benzoimidazole-5-carboxylate (0.2492 g, 8.326×10$^{-4}$ mol), benzyltrimethylammonium dichloroiodinate (Aldrich, 95%, 0.3934 g, 0.00113 mol), and zinc chloride (0.1899 g, 0.00139 mol) in glacial acetic acid (20 ml) was brought to reflux for 15 minutes. The hot suspension was filtered to isolate the precipitate which was dried in the vacuum oven (90° C., ca. 10 mm Hg) overnight to afford 0.2392 g of a green powder; 68% yield; m.p. 219–220° C. DEC; $^1$H-NMR (400 MHz; DMSO) δ8.71 (s, 1H), 8.02 (s, 1H), 7.85 (broad s, 1H), 7.43 (d, 1H, J=1.7 Hz), 7.24 (dd, 1H, J=8.5, 2.2 Hz), 6.24 (dd, 1H, J=8.5, 5.4 Hz), 3.76 (s, 3H), 2.22 (s, 3H); $^{19}$F-NMR (376 MHz; DMSO) δ–132.86 (s); MS (APCl+) 426 (M+1, 48), 169 (100); (APCl–) 424 (M–1, 100); IR (KBr) 1704, 1508, 1227 cm$^{-1}$.

Step h: Preparation of 7-fluoro-6-(4-iodo-2-methyl-phenylamino)-1H-benzoimidazole-5-carboxylic acid To a stirring solution comprised of methyl 7-fluoro-6-(4-iodo-2-methyl-phenylamino)-1H-benzoimidazole-5-carboxylate (0.2035 g, 4.786×10$^{-4}$ mol) in tetrahydrofuran (20 ml) was added solid potassium trimethylsilanolate (0.315 g, 0.00246 mol). The reaction mixture was stirred at ambient temperature under argon for 16 hours. An additional 0.082 g (6.39×10$^{-4}$ mol) of potassium trimethylsilanolate was added and the mixture stirred 30 minutes. The reaction mixture was concentrated in vacuo to one-third volume and was treated with diethyl ether (50 ml). The off-white precipitate formed was collected by vacuum filtration, giving a hygroscopic solid. The wet solid was dissolved in a 4:1 (v/v) ethyl acetate-methanol solution (500 ml). The solution was washed with 0.84 M aqueous citric acid (50 ml), dried (MgSO$_4$), and concentrated in vacuo to a yellow liquid. The liquid was redissolved in fresh ethyl acetate-methanol. The solution was washed with brine, dried (MgSO$_4$), and concentrated in vacuo. The residue was redissolved in chloroform and reconcentrated to afford 1.55 g of a viscous yellow residue which was comprised mainly of citric acid; MS (APCl–) 191 (M–1, 100). The residue was dissolved in water (50 ml). Insoluble material was extracted into 1:1 (v/v)ethyl acetate-diethyl ether (250 ml). Upon separation, the aqueous phase remained strongly acidic (pH 0). The organic phase was washed with a fresh portion of water (150 ml). Upon separation, this wash was only slightly acidic (pH 4.5). The organic phase was dried (MgSO$_4$), concentrated in vacuo, and chased with chloroform to give a tan semisolid. The product was triturated with hexanes. Vacuum filtration and suction-drying afforded 0.0839 g of a tan powder. A portion of the product (0.050 g) was recrystallized from boiling ethanol (1 ml). While cooling and moderate scratching, an off-white solid formed. This product was isolated by vacuum filtration and dried under high vacuum (23° C.) to afford 0.018 g of an off-white powder; 9% yield; m.p. 247–248° C. DEC; $^{19}$F-NMR (376 MHz; DMSO) δ–132.87 (s); MS (APCl+) 412 (M+1,100); (APCl–) 410 (M–1, 100); IR (KBr) 3322, 1689, 1437, 1326, 1218 cm$^{-1}$; Anal. calcd/found for: $C_{15}H_{11}FIN_3O_2$.0.61 $C_2H_6O$ . 0.59 $H_2O$ (91.4% parent) C, 43.30/43.30; H, 3.55/3.34; N, 9.34/9.15.

Example 2

Preparation of 7-fluoro-6-(4-iodo-2-methyl-phenylamino)-1H-benzoimidazole-5-carboxylic acid cyclopropylmethoxy-amide (PD 254552) (APK IC$_{50}$<10 nM (n=2); Colon 26 Cells, 1 Hour Pretreatment, IC$_{50}$=20 nM)

Step a: Preparation of 7-fluoro-6-(4-iodo-2-methyl-phenylamino)-1H-benzoimidazole-5-carboxylic acid pentafluorophenyl ester (PD 254551) (APK IC$_{50}$=120 nM (n=2))

To a stirring suspension comprised of 7-fluoro-6-(4-iodo-2-methyl -phenylamino)-1H-benzoimidazole-5-carboxylic acid (0.844 g, 2.05×10$^{-3}$ mol) in ethyl acetate (4 ml) was added a solution comprised of pentafluorophenol (0.375 g, 2.04×10$^{-3}$ mol) in N,N-dimethylformamide (10 ml). Solid dicyclohexylcarbodiimide (0.415 g, 1.99×10$^{-3}$ mol) was then added and the reaction mixture was stirred for 22 hours. The reaction mixture was vacuum filtered to remove the precipitate that had formed. The filtrate was diluted with ethyl acetate (400 ml), and that solution was washed with water (3×400 ml), was dried (MgSO$_4$), and was concentrated in vacuo to afford 1.7 g of a yellow foam. The crude product was purified by flash silica column chromatography. Elution with a gradient (CHCl$_3$ to 0.5% methanol in CHCl$_3$) afforded 0.69 g of the yellow amorphous product; 60% yield; $^1$H-NMR (400 MHz; CDCl$_3$) δ8.54 (s, 1H), 8.28 (s, 1H), 8.04 (s, 1H), 7.49 (d, 1H, J=1.7 Hz), 7.36 (dd, 1H, J=8.2, 1.7 Hz), 6.57 (dd, 1H, J=8.4, 6.5 Hz), 2.31 (s, 3H); $^{19}$F-NMR (376 MHz; CDCl$_3$) δ–132.02 (s), –152.35 (d, J=18.3 Hz), –157.26 (t, J=21.4 Hz), –161.96 (dd, J=21.3, 18.3 Hz); MS (APCl+) 578 (M+1, 57), 394 (100); (APCl–) 576 (M–1, 44), 409 (100), 393 (95), 392 (82) 378 (55), 183 (97), 165 (68), 127 (53); IR (KBr) 1731 cm$^{-1}$ (C=O stretch).

Step b: Preparation of 7-fluoro-6-(4-iodo-2-methyl-phenylamino)-1H-benzoimidazole-5-carboxylic acid cyclopropylmethoxy-amide To a stirring solution comprised of 7-fluoro-6-(4-iodo-2-methyl -phenylamino)-1H-benzoimidazole-5-carboxylic acid pentafluorophenyl ester (0.63 g, 1.09×10$^{-3}$ mol) in anhydrous tetrahydrofuran (5 ml) was added solid cyclopropylmethoxylamine hydrochloride (0.14 g, 1.13×10$^{-3}$ mol) and diisopropylethylamine (0.6 ml, 3.4×10$^{-3}$ mol). The reaction mixture was stirred for one week. The solvent was removed and the evaporate was treated with 10% aqueous hydrochloric acid (200 ml) and was extracted with diethyl ether (200 ml). A biphasic suspension resulted, and the precipitate was isolated by vacuum filtration. The crude product was recrystallized from absolute ethanol to afford 0.18 g of a green-yellow powder; 35% yield; mp 168–172° C.; $^1$H-NMR (400 MHz; DMSO) δ11.48 (s, 1H), 8.37 (s, 1H), 7.50 (broad s, 1H), 7.45 (s, 1H), 7.24 (s, 1H), 7.07 (d, 1H, J=8.4 Hz), 6.03–5.97 (m, 1H), 3.38 (d, 2H, J=6.5 Hz), 2.04 (s, 3H), 0.85–0.75 (m, 1H), 0.30–0.22 (m, 2H), 0.00 (s, 2H); $^{19}$F-NMR (376 MHz; DMSO) δ–133.23 (s); MS (APCl+) 481 (M+1, 77), 409 (100); (APCl–) 480 (M, 22), 407 (100); IR (KBr) 1659, 1632, 1493 cm$^{-1}$; Anal. calcd/found for: $C_{19}H_{18}FIN_4O_2$. 0.50 HCl (96.3% parent) C, 45.78/45.74; H, 3.74/3.84; N, 11.24/10.88.

Example 3

Preparation of 7-fluoro-6-(4-iodo-2-methyl-phenylamino)-1H-benzoimidazole-5-carboxylic acid hydroxyamide Step a: Preparation of 7-fluoro-6-(4-iodo-2-methyl-phenylamino)-1H-benzoimidazole-5-carboxylic acid O-(tetrahydro-2H-pyran-2-yl)-oxyamide A solution comprised of 7-fluoro-6-(4-iodo-2-methyl-phenylamino)-1H-benzoimidazole-5-carboxylic acid, O-(tetrahydro-2H-pyran-2-yl)-hydroxylamine (1.25 equiv.), benzotriazole-1-yl-oxy-tris-pyrrolidino-phosphonium hexafluorophosphate (1.25 equiv.), and diisopropylethylamine (3 equiv.) in 1:1 v/v tetrahydrofuran-dichloromethane is stirred for 30 minutes. The reaction mixture is concentrated in vacuo and the residue is purified by flash chromatography; elution with dichloromethane affords the desired product. The product may be recrystallized with an appropriate solvent like methanol if further purification is necessary.

Step b: Preparation of 7-fluoro-6-(4-iodo-2-methyl-phenylamino)-1H-benzoimidazole-5-carboxylic acid hydroxyamide The compound 7-fluoro-6-(4-iodo-2-methyl-phenylamino)-1H-benzoimidazole-5-carboxylic acid O-(tetrahydro-2H-pyran-2-yl)-oxyamide is dissolved in an appropriate hydrogen chloride-saturated solvent like methanol or ethanol. Once homogeneous, the solution is concentrated in vacuo to give the desired product. The product may be triturated with an appropriate solvent like chloroform or dichloromethane if further purification is necessary.

Example 4

Preparation of 7-fluoro-6-(4-iodo-2-methyl-phenylamino)-1H-benzoimidazole-5-carboxylic acid cyclopropylmethoxy-amide Step a: Preparation of O-cyclopropylmethylhydroxylamine hydrochloride Step i: Preparation of 2-cyclopropylmethoxy-isoindole-1,3-dione To a stirring solution/suspension comprised of N-hydroxyphthalimide (Aldrich, 57.15 g, 339.8 mmol), cyclopropanemethanol (Aldrich, 25.10 g, 341.1 mmol), and triphenylphosphine ("DEAD," Aldrich, 91.0 g, 344 mmol) in 1.00 L of tetrahydrofuran under a nitrogen atmosphere and cooled to 6° C. (internal mixture temperature) with an ice-water bath was added diethyl azodicarboxylate (Aldrich, 56 ml, 356 mmol) dropwise over 20 minutes via addition funnel. The reaction mixture temperature was kept below 20° C. during the addition. Following addition of the DEAD, the cold bath was removed and the reaction mixture was stirred for 15 hours. The mixture was concentrated to a paste under reduced pressure. Chloroform (ca. 300 ml) was added and the mixture swirled to loosen all solids. Vacuum filtration removed the insolubles. The filtrate was likewise filtered to remove white precipitate that formed and to give a clear filtrate. Concentration under reduced pressure afforded a clear oil. Flash filtration through silica gel (100% chloroform) gave filtrates containing unseparated product. These filtrates were combined and concentrated under reduced pressure to afford 127.4 g of a clear oil. The oil was dissolved in absolute ethanol (400 ml) and the solution was refrigerated for two hours. A white crystalline solid had precipitated and was subsequently collected by vacuum filtration. The product was dried in the vacuum oven (60° C.) to afford 42.66 g (58%) of the desired material; m.p. 71–77° C.; $^1$H-NMR (400 MHz; CDCl$_3$ signal offset to δ6.96) δ7.54–7.43 (m, 4H), 3.74 (d, 2H, J=7.6 Hz), 1.02–0.95 (m, 1H), 0.34–0.30 (m, 1H) 0.04–0.00 (m, 1H).

Step ii: Preparation of O-cyclopropylmethylhydroxylamine hydrochloride

To a stirring solution comprised of 2-cyclopropylmethoxy-isoindole-1,3-dione (42.64 g, 196.3 mmol) in 150 ml of dichloromethane under ambient conditions was carefully added methylhydrazine (Aldrich, 10.7 ml, 197 mmol). A white precipitate began to form almost instantly. After 15 minutes of vigorous stirring, the suspension was vacuum filtered. The filtrate was likewise filtered to remove additional precipitate. The resulting clear filtrate was concentrated carefully (volatile product) under reduced pressure to afford a clear liquid/solid mixture. The white solids were removed when an ether (200 ml) solution of the product was made and vacuum filtered. The filtrate was acidified with gaseous hydrogen chloride, affording instantly a white precipitate. Collection of the solid by vacuum filtration and vacuum-oven drying (55° C.) afforded 18.7 g (77%) of the white powder product; m.p. 165–168° C.; $^1$H-NMR (400 MHz; DMSO) δ10.77 (broad s, 2H), 3.57 (d, 2H, J=7.3 Hz), 0.84–0.74 (m, 1H), 0.31–0.25 (m, 2H), 0.04–0.00 (m, 1H); $^{13}$C-NMR (100 MHz; DMSO) δ75.39, 5.52, 0.00.

Step b: Preparation of 7-fluoro-6-(4-iodo-2-methyl-phenylamino)-1H-benzoimidazole-5-carboxylic acid cyclopropylmethoxy-amide A solution comprised of 7-fluoro-6-(4-iodo-2-methyl-phenylamino)-1H-benzoimidazole-5-carboxylic acid, O-cyclopropylmethylhydroxylamine hydrochloride (1.25 equiv.), benzotriazole-1-yl-oxy-tris-pyrrolidino-phosphonium hexafluorophosphate (1.25 equiv.), and diisopropylethylamine (3 equiv.) in 1:1 v/v tetrahydrofuran-dichloromethane is stirred for 30 minutes. The reaction mixture is concentrated in vacuo and the residue is taken up into diethyl ether. The ether phase is washed with dilute aqueous hydrochloric acid, saturated aqueous sodium bicarbonate, and brine, is dried (MgSO$_4$), and is concentrated in vacuo to afford the desired product. The product may be recrystallized with an appropriate solvent like methanol or chloroform if further purification is necessary.

Example 5

Preparation of 7-fluoro-6-(4-iodo-2-methyl-phenylamino)-1H-benzooxazole-5-carboxylic acid Step a: Preparation of 5-nitro-2,3,4-trifluorobenzoic acid
  Same as for Example 1, Step a.

Step b: Preparation of 2,3-difluoro4-hydroxy-5-nitrobenzoic acid

The solid 5-nitro-2,3,4-trifluorobenzoic acid (1.00 g, 0.00452 mol) was dissolved in 10 wt. % aqueous sodium hydroxide solution. The mixture was clear deep orange. After standing under ambient conditions for several minutes, the mixture was quenched with concentrated aqueous hydrochloric acid until strongly acidic (pH 0). A white solid precipitated which was isolated by vacuum filtration and dried with suction to afford 0.40 g of an off-white solid. This solid was recrystallized from chloroform (20 ml) to afford 0.22 g of an off-white crystalline powder; 22% yield; MS (APCl−) 218 (M−1, 100).

Step c: Preparation of methyl 2,3-difluoro-4-hydroxy-5-nitrobenzoate

Anhydrous hydrogen chloride gas was dissolved in anhydrous methanol (50 ml) until the solution was warm. The microcrystalline solid 2,3-difluoro-4-hydroxy-5-nitrobenzoic acid 0.22 g, 0.00100 mol) was dissolved in the methanolic hydrogen chloride solution. The stirring reaction mixture was brought to reflux under nitrogen for 16 hours. The mixture was concentrated in vacuo to give a white solid. The product was dried under high vacuum to afford 0.213 g of a white powder; 91% yield; m.p. 108–109.5° C.; $^1$H-NMR (400 MHz; DMSO) δ8.25 (dd, 1H, J=7.7, 2.2 Hz), 3.83 (s, 3H); (CDCl$_3$) δ10.83 (s, 1H), 8.66 (dd, 1H, J=7.0, 2.2 Hz), 3.98 (s, 3H); $^{19}$F-NMR (376 MHz; DMSO) δ−127.85 (s), −154.32 (d, J=19.8 Hz); (CDCl$_3$) δ −118.31 to −118.37 (m), −152.38 (d, J=18.3 Hz); MS (APCl−) 232 (M−1, 100); IR (KBr) 3264, 1731, 1640, 1546, 1307, 1286, 1160 cm$^{-1}$.

Step d: Preparation of 1-adamantyl 4-carboxymethyl-2,3-difluoro-6-nitrophenyl carbonate To a solution comprised of 1-adamantyl fluoroformate (2.0 M) and pyridine (2.0 M) in tetrahydrofuran is added a stirred solution comprised of methyl 2,3-difluoro-4-hydroxy-5-nitrobenzoate (0.96 equiv., 0.384 M) in anhydrous tetrahydrofuran at ambient temperature. The reaction mixture is stirred for 6 hours and the solvent is removed in vacuo. The residue is dissolved in dichloromethane. The organic solution is washed with dilute aqueous hydrochloric acid, dilute aqueous sodium carbonate, and water, is dried (MgSO$_4$), and is concentrated in vacuo to give the desired product. ps Step e: Preparation of 1-adamantyl 4-carboxymethyl-2-fluoro-3-(2-methyl-phenylamino)-6-nitrophenyl carbonate The compound 1-adamantyl 4-carboxymethyl-2,3-difluoro-6-nitrophenyl carbonate is dissolved in excess ortho-toluidine. The reaction mixture is stirred at 200° C. for 6 hours. The mixture is allowed to cool and is dissolved in diethyl ether. The organic phase is washed with dilute aqueous hydrochloric acid, saturated aqueous sodium bicarbonate, and brine, is dried (MgSO$_4$), and is concentrated in vacuo to afford the desired product. The product is purified by flash chromatography as necessary.

Step f: Preparation of methyl 3-fluoro-4-hydroxy-2-(2-methyl-phenylamino)-5-nitrobenzoate The compound 1-adamantyl 4-carboxymethyl-2-fluoro-3-(2-methyl-phenylamino)-6-nitrophenyl carbonate is dissolved in excess trifluoroacetic acid at ambient temperature. The mixture is stirred for 20 minutes. The TFA is removed under reduced pressure. The residue is subjected to vacuum pump to remove adamantan-1-ol to give the desired product.

Step g: Preparation of methyl 5-amino-3-fluoro-4-hydroxy-2-(2-methyl-phenylamino)-benzoate The compound methyl 3-fluoro-4-hydroxy-2-(2-methyl-phenylamino)-5-nitrobenzoate is treated as in Step e, Example 1.

Step h: Preparation of methyl 7-fluoro-6-(2-methyl-phenylamino)-1H-benzooxazole-5-carboxylate The compound 5-amino-3-fluoro-4-hydroxy-2-(2-methyl-phenylamino)-benzoate is treated as in Step f, Example 1. The product may be recrystallized with an appropriate solvent like chloroform or ethanol if further purification is necessary.

Step i: Preparation of methyl 7-fluoro-6-(4-iodo-2-methyl-phenylamino)-1H-benzooxazole-5-carboxylate A stirring mixture comprised of methyl 7-fluoro-6-(2-methyl-phenylamino)-1H-benzooxazole-5-carboxylate (0.042 M), benzyltrimethylammonium dichloroiodinate (Aldrich, 95%, 0.057 M, 1.36 equiv.), and zinc chloride (0.070 M, 1.67 equiv.) in glacial acetic acid is brought to reflux for 15 minutes. The mixture is concentrated in vacuo and the residue taken up into diethyl ether. The ether solution is washed with dilute aqueous hydrochloric acid, water, and brine, is dried (MgSO$_4$), and is concentrated in vacuo to obtain the desired product. The product may be purified by recrystallization with an appropriate solvent like ethanol.

Step j: Preparation of 7-fluoro-6-(4-iodo-2-methyl-phenylamino)-1H-benzooxazole-5-carboxylic acid To a stirring solution comprised of methyl 7-fluoro-6-(4-iodo-2-methyl-phenylamino)-1H-benzooxazole-5-carboxylate (0.024 M) in tetrahydrofuran is added solid potassium trimethylsilanolate (5.14 equiv.). The reaction mixture is stirred at ambient temperature under argon for 16 hours. An additional equivalent of potassium trimethylsilanolate is added and the mixture stirred 30 minutes. The reaction mixture is concentrated in vacuo to give a residue that is then taken up into 1:1 (v/v)ethyl acetate-diethyl ether. The organic phase is washed with dilute aqueous hydrochloric acid, water, and brine, is dried (MgSO$_4$), is concentrated in vacuo, and chased with chloroform to give a crude product. Recrystallization from an appropriate solvent like ethanol gives the purified desired product. cl Example 6

Preparation of 7-fluoro-6-(4-iodo-2-methyl-phenylamino)-1H-benzooxazole-5-carboxylic acid hydroxyamide Step a: Preparation of 7-fluoro-6-(4-iodo-2-methyl-phenylamino)-1H-benzooxazole-5-carboxylic acid O-(tetrahydro-2H-pyran-2-yl)-oxyamide The compound 7-fluoro-6-(4-iodo-2-methyl-phenylamino)-1H-benzooxazole-5-carboxylic acid is treated as in Step a, Example 2.

Step b: Preparation of 7-fluoro-6-(4-iodo-2-methyl-phenylamino)-1H-benzooxazole-5-carboxylic acid hydroxyamide The compound 7-fluoro-6-(4-iodo-2-methyl-phenylamino)-1H-benzooxazole-5-carboxylic acid O-(tetrahydro-2H-pyran-2-yl)-oxyamide is treated as in Step b, Example 2.

Example 7

Preparation of 7-fluoro-6-(4-iodo-2-methyl-phenylamino)-1H-benzooxazole-5-carboxylic acid cyclopropylmethoxy-amide The compound 7-fluoro-6-(4-iodo-2-methyl-phenylamino)-1H-benzooxazole-5-carboxylic acid is treated as in Step b, Example 3.

Example 8

Preparation of 7-fluoro-6-(4-iodo-2-methyl-phenylamino)-1H-benzothiazole-5-carboxylic acid Step a: Preparation of 5-nitro-2,3,4-trifluorobenzoic acid

39

Same as for Example 1, Step a.
Step b: Preparation of 2,3-difluoro-4-hydroxy-5-nitrobenzoic acid
Same as for Example 4, Step b.
Step c: Preparation of methyl 2,3-difluoro-4-hydroxy-5-nitrobenzoate
Same as for Example 4, Step c.
Step d: Preparation of 4-dimethylthiocarbamoyloxy-2,3-difluoro-5-nitro-benzoic acid methyl ester A solution of methyl 2,3-difluoro-4-hydroxy-5-nitrobenzoate in N,N-dimethylformamide is treated with one molar equivalent of cesium carbonate and warmed to 85° C. for 30 minutes. The stirring mixture is then treated dropwise rapidly with a solution comprised of a slight excess of N,N-dimethylthiocarbamoyl chloride in N,N-dimethylformamide. The reaction mixture is stirred at room temperature for one hour, or may be warmed over a steam bath for one hour. The mixture is then poured into water and extracted with ethyl acetate. The organic phase is washed with 5% aqueous sodium hydroxide, water, and brine, and is then dried with a drying agent like magnesium sulfate of sodium sulfate. The solvent is then removed in vacuo to give a crude product. The compound is purified by ordinary methods such as chromatography or crystallization from an appropriate solvent.
Step e: Preparation of 4-Dimethylthiocarbamoyloxy-3-fluoro-5-nitro-2-o-tolylamino-benzoic acid methyl ester The compound 4-dimethylthiocarbamoyloxy-2,3-difluoro-5-nitro-benzoic acid methyl ester is dissolved in excess o-toluidine. The stirring mixture is brought to 200° C. for one hour. The mixture is then poured into 5% aqueous hydrochloric acid. The aqueous mixture is extracted with diethyl ether. The organic phase is washed with water and brine, is dried over magnesium sulfate, and is concentrated in vacuo. The crude product is purified by ordinary methods such as chromatography or crystallization from an appropriate solvent.
Step f: Preparation of methyl 7-fluoro-6-(2-methyl-phenylamino)-1H-benzothiazole-5-carboxylate The compound methyl 5-amino-3-fluoro-4-mercapto-2-(2-methyl-phenylamino)-benzoate is treated as in Step h, Example 4.
Step g: Preparation of methyl 7-fluoro-6-(4-iodo-2-methyl-phenylamino)-1H-benzothiazole-5-carboxylate The compound methyl 7-fluoro-6-(2-methyl-phenylamino)-1H-benzothiazole-5-carboxylate is treated as in Step i, Example 4.
Step h: Preparation of 7-fluoro-6-(4-iodo-2-methyl-phenylamino)-1H-benzothiazole-5-carboxylic acid The compound methyl 7-fluoro-6-(4-iodo-2-methyl-phenylamino)-1H-benzothiazole-5-carboxylate is treated as in Step j, Example 4.

Example 9

Preparation of 7-fluoro-6-(4-iodo-2-methyl-phenylamino)-1H-benzothiazole-5-carboxylic acid hydroxyamide Step a: Preparation of 7-fluoro-6-(4-iodo-2-methyl-phenylamino)-1H-benzothiazole-5-carboxylic acid O-(tetrahydro-2H-pyran-2-yl)-oxyamide The compound 7-fluoro-6-(4-iodo-2-methyl-phenylamino)-1H-benzothiazole-5-carboxylic acid is treated as in Step a, Example 2.
Step b: Preparation of 7-fluoro-6-(4-iodo-2-methyl-phenylamino)-1H-benzothiazole-5-carboxylic acid hydroxyamide The compound 7-fluoro-6-(4-iodo-2-methyl-phenylamino)-1H-benzothiazole-5-carboxylic acid O-(tetrahydro-2H-pyran-2-yl)-oxyamide is treated as in Step b, Example 2.

40

Example 10

Preparation of 7-fluoro-6-(4-iodo-2-methyl-phenylamino)-1H-benzothiazole-5-carboxylic acid cyclopropylmethoxy-amide The compound 7-fluoro-6-(4-iodo-2-methyl-phenylamino)-1H-benzothiazole-5-carboxylic acid is treated as in Step b, Example 3.

Example 11

Preparation of 8-fluoro-7-(4-iodo-2-methyl-phenylamino)-quinoxaline-6-carboxylic acid
Step a: Preparation of 8-fluoro-7-(2-methyl-phenylamino)-quinoxaline-6-carboxylic acid The compound methyl 4,5-diamino-3-fluoro-2-(2-methyl-phenylamino)-benzoate (from Step e, Example 1) is dissolved in 2:1:1.2 v/v/v of 2.0 M acetic acid-4.0 M sodium acetate-methanol. The suspension is warmed to 65° C. (or until homogeneous) and the clear solution is poured into a 0.078 M aqueous sodium glyoxal bisulfite (Aldrich, monohydrate, 1.05 equiv.) solution which is warmed to 70° C. The reaction mixture is stirred gently between 55–75° C. for one hour, and is then cooled to 12° C. with an ice-water bath. Pulverized sodium hydroxide pellets (27 equiv.) are added to the cold solution. The mixture is gently warmed to 30° C. and stirred for 45 minutes. The temperature is raised to 70° C. for 15 minutes. The mixture is allowed to cool and is treated with ethyl acetate. The biphasic mixture is treated with concentrated aqueous hydrochloric acid to achieve pH 0 in the aqueous phase. The organic phase is separated, dried ($MgSO_4$), and concentrated in vacuo to give the desired product. The product may be triturated with an appropriate solvent like dichloromethane or recrystallized from a solvent like ethanol for further purification as necessary.
Step b: Preparation of 8-fluoro-7-(4-iodo-2-methyl-phenylamino)-quinoxaline-6-carboxylic acid The compound 8-fluoro-7-(2-methyl-phenylamino)-quinoxaline-6-carboxylic acid is treated as in Step i, Example 4.

Example 12

Preparation of 8-fluoro-7-(4-iodo-2-methyl-phenylamino)-quinoxaline-6-carboxylic acid hydroxyamide
Step a: Preparation of 8-fluoro-7-(4-iodo-2-methyl-phenylamino)-quinoxaline-6-carboxylic acid O-(tetrahydro-2H-pyran-2-yl)-oxyamide The compound 8-fluoro-7-(4-iodo-2-methyl-phenylamino)-quinoxaline-6-carboxylic acid is treated as in Step a, Example 2.
Step b: Preparation of 8-fluoro-7-(4-iodo-2-methyl-phenylamino)-quinoxaline-6-carboxylic acid hydroxyamide The compound 8-fluoro-7-(4-iodo-2-methyl-phenylamino)-quinoxaline-6-carboxylic acid O-(tetrahydro-2H-pyran-2-yl)-oxyamide is treated as in Step b, Example 2.

Example 13

Preparation of 8-fluoro-7-(4-iodo-2-methyl-phenylamino)-quinoxaline-6-carboxylic acid cyclopropylmethoxyamide The compound 8-fluoro-7-(4-iodo-2-methyl-phenylamino)-quinoxaline-6-carboxylic acid is treated as in Step b, Example 3.

Example 14

Preparation of 7-fluoro-6-(4-iodo-2-methyl-phenylamino)-benzo[1,2,5]thiadiazole-5-carboxylic acid
Step a: Preparation of methyl 7-fluoro-6-(2-methyl-phenylamino)-benzo[1,2,5]thiadiazole-5-carboxylate To a stirring solution comprised of methyl 4,5-diamino-3-fluoro-2-(2-methyl-phenylamino)-benzoate (from Step e, Example 1) and diisopropylethylamine (2 equiv.) in an appropriate solvent like diethyl ether or toluene is added a reagent like N-thioaniline or thionyl chloride (1.35 equiv.). The reaction mixture is brought to reflux for one hour. The mixture is quenched with dilute aqueous hydrochloric acid. The organic phase is washed with saturated aqueous sodium bicarbonate and brine, is dried ($MgSO_4$), and is concentrated in vacuo to afford the desired product. The product may be recrystallized with an appropriate solvent like chloroform or ethanol, or may be chromatographed if further purification is necessary.

Alternative Method:

The compound methyl 4,5-diamino-3-fluoro-2-(2-methyl-phenylamino)-benzoate is added to a stirring solution of sulfur monochloride (6 equiv.) in N,N-dimethylformamide and the mixture is gradually heated to 75–80° C. After 5 hours the mixture is cooled to 10° C., water is slowly added. The mixture is extracted with a solvent like diethyl ether or dichloromethane. The organic extract is dried ($MgSO_4$) and is concentrated in vacuo to afford the desired product. The product may be recrystallized with an appropriate solvent like chloroform or ethanol, or may be chromatographed if further purification is necessary.

Step b: Preparation of methyl 7-fluoro-6-(4-iodo-2-methyl-phenylamino)-benzo[1,2,5]thiadiazole-5-carboxylate The compound methyl 7-fluoro-6-(2-methyl-phenylamino)-benzol[1,2,5]thiadiazole-5-carboxylate is treated as in Step i, Example 4.

Step c: Preparation of 7-fluoro-6-(4-iodo-2-methyl-phenylamino)-benzo[1,2,5]thiadiazole-5-carboxylic acid The compound methyl 7-fluoro-6-(4-iodo-2-methyl-phenylamino)-benzo[1,2,5]thiadiazole-5-carboxylate is treated as in Step j, Example 4.

Example 15

Preparation of 7-fluoro-6-(4-iodo-2-methyl-phenylamino)-benzo[1,2,5]thiadiazole-5-carboxylic acid hydroxyamide Step a: Preparation of 7-fluoro-6-(4-iodo-2-methyl-phenylamino)-benzo[1,2,5]thiadiazole-5-carboxylic acid O-(tetrahydro-2H-pyran-2-yl)-oxyamide The compound 7-fluoro-6-(4-iodo-2-methyl-phenylamino)-benzo[1,2,5]thiadiazole-5-carboxylic acid is treated as in Step a, Example 2.

Step b: Preparation of 7-fluoro-6-(4-iodo-2-methyl-phenylamino)-benzo[1,2,5]thiadiazole-5-carboxylic acid hydroxyamide The compound 7-fluoro-6-(4-iodo-2-methyl-phenylamino)-benzo[1,2,5]thiadiazole-5-carboxylic acid O-(tetrahydro-2H-pyran-2-yl)-oxyamide is treated as in Step b, Example 2.

Example 16

Preparation of 7-fluoro-6-(4-iodo-2-methyl-phenylamino)-benzo[1,2,5]thiadiazole-5-carboxylic acid cyclopropylmethoxy-amide The compound 7-fluoro-6-(4-iodo-2-methyl-phenylamino)-benzo[1,2,5]thiadiazole-5-carboxylic acid is treated as in Step b, Example 3.

Example 17

Preparation of 7-fluoro-6-(4-iodo-2-methyl-phenylamino)-benzo[1,2,5]oxadiazole-5-carboxylic acid Step a: Preparation of methyl 7-fluoro-6-(2-methyl-phenylamino)-benzo[1,2,5]oxadiazole-5-carboxylate 2-oxide See Takakis, I. M.; Hadjimihalakis, P. M., *J. Heterocyclic Chem.*, 27, 177 (1 990).

A mixture comprised of methyl 4-amino-3-fluoro-2-(2-methyl-phenylamino)-5-nitrobenzoate (from Step d, Example 1) and iodosobenzenediacetate (1.76 equiv.) in benzene is stirred at ambient temperature for 5 hours. The mixture is concentrated in vacuo and the residue purified by column chromatography to give the desired product.

Alternative Method:

A solution comprised of methyl 4-amino-3-fluoro-2-(2-methyl-phenylamino)-5-nitrobenzoate (0.86 M) in tetrahydrofuran is diazotized and the diazonium salt is treated in situ with sodium azide as described by Smith, P. A. S.; Boyer, J. H., *Org. Synth.*, 31, 14 (1951) and references 4 and 8 cited therein. Thermolysis of this intermediate in ethylene glycol at 110–120° C. for one hour affords the desired product.

Step b: Preparation of methyl 7-fluoro-6-(2-methyl-phenylamino)-benzo[1,2,5]oxadiazole-5-carboxylate A solution comprised of methyl 7-fluoro-6-(2-methyl-phenylamino)-benzo[1,2,5]oxadiazole-5-carboxylate 2-oxide and sodium azide (1.38 equiv.) in ethylene glycol is heated to 140–150° C. for 30 minutes to obtain, after column chromatography, the desired product.

Step c: Preparation of methyl 7-fluoro-6-(4-iodo-2-methyl-phenylamino)-benzo[1,2,5]oxadiazole-5-carboxylate The compound methyl 7-fluoro-6-(2-methyl-phenylamino)-benzo[1,2,5]oxadiazole-5-carboxylate is treated as in Step i, Example 4.

Step d: Preparation of 7-fluoro-6-(4-iodo-2-methyl-phenylamino)-benzo[1,2,5]oxadiazole-5-carboxylic acid The compound methyl 7-fluoro-6-(4-iodo-2-methyl-phenylamino)-benzo[1,2,5]oxadiazole-5-carboxylate is treated as in Step j, Example 4.

Example 18

Preparation of 7-fluoro-6-(4-iodo-2-methyl-phenylamino)-benzo[1,2,5]oxadiazole-5-carboxylic acid hydroxyamide Step a: Preparation of 7-fluoro-6-(4-iodo-2-methyl-phenylamino)-benzo[1,2,5]oxadiazole-5-carboxylic acid O-(tetrahydro-2H-pyran-2-yl)-oxyamide The compound 7-fluoro-6-(4-iodo-2-methyl-phenylamino)-benzo[1,2,5]oxadiazole-5-carboxylic acid is treated as in Step a, Example 2.

Step b: Preparation of 7-fluoro-6-(4-iodo-2-methyl-phenylamino)-benzo[1,2,5]oxadiazole-5-carboxylic acid hydroxyamide The compound 7-fluoro-6-(4-iodo-2-methyl-phenylamino)-benzo[1,2,5]oxadiazole-5-carboxylic acid O-(tetrahydro-2H-pyran-2-yl)-oxyamide is treated as in Step b, Example 2.

Example 19

Preparation of 7-fluoro-6-(4-iodo-2-methyl-phenylamino)-benzo[1,2,5]oxadiazole-5-carboxylic acid cyclopropylmethoxy-amide The compound 7-fluoro-6-(4-iodo-2-methyl-phenylamino)-benzo[1,2,5]oxadiazole-5-carboxylic acid is treated as in Step b, Example 3.

Example 20

Preparation of 7-fluoro-6-(4-iodo-2-methyl-phenylamino)-1H-benzotriazole-5-carboxylic acid Step a: Preparation of methyl 7-fluoro-6-(2-methyl-phenylamino)-1H-benzotriazole-5-carboxylate The compound methyl 4,5-diamino-3-fluoro-2-(2-methyl-phenylamino)-benzoate (from Step e, Example 1) is diazotized by ordinary methods. Workup gives the desired product.

Step b: Preparation of methyl 7-fluoro-6-(4-iodo-2-methyl-phenylamino)-1H-benzotriazole-5-carboxylate The compound methyl 7-fluoro-6-(2-methyl-phenylamino)-1H-benzotriazole-5-carboxylate is treated as in Step i, Example 4.

Step c: Preparation of 7-fluoro-6-(4-iodo-2-methyl-phenylamino)-1H-benzotriazole-5-carboxylic acid The compound methyl 7-fluoro-6-(4-iodo-2-methyl-phenylamino)-1H-benzotriazole-5-carboxylate is treated as in Step j, Example 4.

Example 21

Preparation of 7-fluoro-6-(4-iodo-2-methyl-phenylamino)-1H-benzotriazole-5-carboxylic acid hydroxyamide Step a: Preparation of 7-fluoro-6-(4-iodo-2-methyl-phenylamino)-1H-benzotriazole-5-carboxylic acid O-(tetrahydro-2H-pyran-2-yl)-oxyamide The compound 7-fluoro-6-(4-iodo-2-methyl-phenylamino)-1H-benzotriazole-5-carboxylic acid is treated as in Step a, Example 2.

Step b: Preparation of 7-fluoro-6-(4-iodo-2-methyl-phenylamino)-1H-benzotriazole-5-carboxylic acid hydroxyamide The compound 7-fluoro-6-(4-iodo-2-methyl-phenylamino)-1H-benzotriazole-5-carboxylic acid O-(tetrahydro-2H-pyran-2-yl)-oxyamide is treated as in Step b, Example 2.

Example 22

Preparation of 7-fluoro-6-(4-iodo-2-methyl-phenylamino)-1H-benzotriazole-5-carboxylic acid cyclopropylmethoxy-amide The compound 7-fluoro-6-(4-iodo-2-methyl-phenylamino)-1H-benzotriazole-5-carboxylic acid is treated as in Step b, Example 3.

Example 23

Cascade Assay for Inhibitors of the MAP Kinase Pathway

Incorporation of $^{32}$P into myelin basic protein (MBP) is assayed in the presence of a glutathione S-transferase fusion protein containing p44MAP kinase (GST-MAPK) and a glutathione S-transferase fusion protein containing p45MEK (GST-MEK). The assay solution contains 20 mM HEPES, pH 7.4, 10 mM MgCl$_2$, 1 mM EGTA, 50 $\mu$M [$\gamma$-$^{32}$P]ATP, 10 $\mu$g GST-MEK, 0.5 $\mu$g GST-MAPK and 40 $\mu$g MBP in a final volume of 100 $\mu$L. Reactions are stopped after 20 minutes by addition of trichloroacetic acid and filtered through a GFIC filter mat. $^{32}$P retained on the filter mat is determined using a 120S Betaplate. Compounds are assessed at 10 $\mu$M for ability to inhibit incorporation of 32P.

To ascertain whether compounds are inhibiting GST-MEK or GST MAPK, two additional protocols are employed. In the first protocol, compounds are added to tubes containing GST-MEK, followed by addition of GST-MAPK, MBP and [$\gamma$-$^{32}$P]ATP. In the second protocol, compounds are added to tubes containing both GST-MEK and GST-MAPK, followed by MBP and [$\gamma$-$^{32}$P]ATP.

Compounds that show activity in both protocols are scored as MAPK inhibitors, while compounds showing activity in only the first protocol are scored as MEK inhibitors.

Example 24

In Vitro MAP Kinase Assay

Inhibitory activity can be confirmed in direct assays. For MAP kinase, 1 $\mu$g GST-MAPK is incubated with 40 $\mu$g MBP for 15 minutes at 30° C. in a final volume of 50 $\mu$L containing 50 mM Tris (pH 7.5), 10 $\mu$M MgCl$_2$, 2 $\mu$M EGTA, and 10 $\mu$M [$\gamma$-$^{32}$P]ATP. The reaction is stopped by addition of Laemmli SDS sample buffer and phosphorylated MBP resolved by electrophoresis on a 10% polyacrylamide gel. Radioactivity incorporated into MBP is determined by both autoradiography, and scintillation counting of excised bands.

Example 25

In Vitro MEK Assay

For evaluation of direct MEK activity, 10 $\mu$g GST-MEK$_1$ is incubated with 5 $\mu$g of a glutathione S-transferase fusion protein containing p44MAP kinase with a lysine to alanine mutation at position 71 (GST-MAPK-KA). This mutation eliminates kinase activity of MAPK, so only kinase activity attributed to the added MEK remains. Incubations are 15 minutes at 30° C. in a final volume of 50 $\mu$L containing 50 mM Tris (pH 7.5), 10 $\mu$M MgCl$_2$, 2, $\mu$M EGTA, and 10 $\mu$M [$\gamma$-$^{32}$P]ATP. The reaction is stopped by addition of Laemmli SDS sample buffer. Phosphorylated GST-MAPK-KA is resolved by electrophoresis on a 10% polyacrylamide gel. Radioactivity incorporated into GST-MAPK-KA is determined by autoradiography, and subsequent scintillation counting of excised bands. Additionally, an artificially activated MEK containing serine to glutamate mutations at positions 218 and 222 (GST-MEK-2E) is used. When these two sites are phosphorylated, MEK activity is increased. Phosphorylation of these sites can be mimicked by mutation of the serine residues to glutamate. For this assay, 5 $\mu$g GST-MEK-2E is incubated with 5 $\mu$g GST-MAPK-KA for 15 minutes at 30° C. in the same reaction buffer as described above. Reactions are terminated and analyzed as above.

Example 26

Whole Cell MAP Kinase Assay

To determine if compounds block activation of MAP kinase in whole cells, the following protocol is used. Cells are plated in multi-well plates and grown to confluence. Cells are serum-deprived overnight. Cells are exposed to the desired concentrations of compound or vehicle (DMSO) for 30 minutes, followed by addition of a growth factor, for example, PDGF (100 ng/mL). After a 5-minute treatment with the growth factor, cells are washed with PBS, and lysed in a buffer consisting of 70 mM NaCl, 10 mM HEPES (pH 7.4), 50 mM glycerol phosphate, and 1% Triton X-100. Lysates are clarified by centrifugation at 13,000×g for 10 minutes. Five to fifteen micrograms of protein from the resulting supernatants are subjected to SDS/PAGE and Western blotting for phosphorylated MAP kinase levels.

Example 27

Monolayer Growth

Cells are plated into multi-well plates at 10 to 20,000 cells/mL. Forty-eight hours after seeding, test compounds are added to the cell growth medium and incubation is continued for 2 additional days. Cells are then removed from the wells by incubation with trypsin and enumerated with a Coulter counter.

Example 28

Growth in Soft-agar

Cells are seeded into 35-mm dishes at 5 to 10,000 cells/dish using growth medium containing 0.3% agar. After chilling to solidify the agar, cells are transferred to a 37° C. incubator. After 7 to 10 days' growth. visible colonies are manually enumerated with the aid of a dissecting microscope.

Example 29
Collagen-induced Arthritis in Mice

Type II collagen-induced arthritis (CIA) in mice is an experimental model of arthritis that has a number of pathologic, immunologic, and genetic features in common with rheumatoid arthritis. The disease is induced by immunization of DBA/1 mice with 100 $\mu$g type II collagen, which is a major component of joint cartilage, delivered intradermally in Freund's complete adjuvant. The disease susceptibility is regulated by the class II MHC gene locus, which is analogous to the association of rheumatoid arthritis with HLA-DR4.

A progressive and inflammatory arthritis develops in the majority of mice immunized, characterized by paw width increases of up to 100%. A test compound is administered to mice in a range of amounts, such as 20, 60, 100, and 200 mg/kg body weight/day. The duration of the test can be several weeks to a few months, such as 40, 60, or 80 days. A clinical scoring index is used to assess disease progression from erythema and edema (stage 1), joint distortion (stage 2), to joint ankylosis (stage 3). The disease is variable in that it can affect one or all paws in an animal, resulting in a total possible score of 12 for each mouse. Histopathology of an arthritic joint reveals synovitis, pannus formation, and cartilage and bone erosions. All mouse strains that are susceptible to CIA are high antibody responders to type II collagen, and there is a marked cellular response to CII.

Example 30
SCW-induced Monoarticular Arthritis

Arthritis is induced as described by Schwab, et al., *Infection and Immunity*, 59:4436–4442 (1991) with minor modifications. Rats receive 6 $\mu$g sonicated SCW [in 10 $\mu$l Dulbecco's PBS (DPBS)] by an intraarticular injection into the right tibiotalar joint on day 0. On day 21, the DTH is initiated with 100 $\mu$g of SCW (250 $\mu$l) administered i.v. For oral compound studies, compounds are suspended in vehicle (0.5% hydroxypropyl-methylcellulose/0.2% Tween 80), sonicated, and administered twice daily (10 ml/kg volume) beginning 1 hr prior to reactivation with SCW. Compounds are administered in amounts between 10 and 500 mg/kg body weight/day, such as 20, 30, 60, 100, 200, and 300 mg/kg/day. Edema measurements are obtained by determining the baseline volumes of the sensitized hindpaw before reactivation on day 21, and comparing them with volumes at subsequent time points such as day 22, 23, 24, and 25. Paw volume is determined by mercury plethysmography.

Example 31
Mouse Ear-heart Transplant Model

Fey, T. A. et al. describe methods for transplanting split-heart neonatal cardiac grafts into the ear pinna of mice and rats (*J. Pharm. and Toxic. Meth.* 39:9–17 (1998)). Compounds are dissolved in solutions containing combinations of absolute ethanol, 0.2% hydroxypropyl methylcellulose in water, propylene glycol, cremophor, and dextrose, or other solvent or suspending vehicle. Mice are dosed orally or intraperitoneally once, twice or three times daily from the day of transplant (day 0) through day 13 or until grafts have been rejected. Rats are dosed once, twice, or three times daily from day 0 through day 13. Each animal is anesthetized and an incision is made at the base of the recipient ear, cutting only the dorsal epidermis and dermis. The incision is spread open and down to the cartilage parallel to the head, and sufficiently wide to accommodate the appropriate tunneling for a rat or insertion tool for a mouse. A neonatal mouse or rat pup less than 60 hours old is anesthetized and cervically dislocated. The heart is removed from the chest, rinsed with saline, bisected longitudinally with a scalpel, and rinsed with sterile saline. The donor heart fragment is placed into the preformed tunnel with the insertion tool and air or residual fluid is gently expressed from the tunnel with light pressure. No suturing, adhesive bonding, bandaging, or treatment with antibiotics is required.

Implants are examined at 10–20-fold magnification with a stereoscopic dissecting microscope without anesthesia. Recipients whose grafts are not visibly beating may be anesthetized and evaluated for the presence of electrical activity using Grass E-2 platinum subdermal pin microelectodes placed either in the pinna or directly into the graft and a tachograph. Implants can be examined 1–4 times a day for 10, 20, 30 or more days. The ability of a test compound to ameliorate symptoms of transplant rejection can be compared with a control compound such as cyclosporine, tacrolimus, or orally-administered lefluonomide.

Example 32
Murine Ovalbumin-induced Eosinophilia

Female C57BL/6 mice are obtained from the Jackson Laboratory (Bar Harbor, Me.). All animals are given food and water ad libitum. Mice are sensitized with a single i.p. injection of OVA (grade V, Sigma Chemical Company, St. Louis, Mo.) adsorbed to alum, (10 $\mu$g OVA+9 mg alum in 200 $\mu$l saline) or vehicle control, (9 mg alum in 200 $\mu$l saline) on day 0. On day 14, the mice are challenged with a 12-minute inhalation of an aerosol consisting of 1.5% OVA (weight/volume) in saline produced by a nebulizer (small particle generator, model SPAG-2; ICN Pharmaceuticals, Costa Mesa, Calif.). Groups of eight mice are dosed with oral vehicle (0.5% hydroxypropylmethylcellulose/0.25% TWEEN-80), or a test compound at 10, 30, or 100 mg/kg in oral vehicle, 200 $\mu$l per mouse p.o. Dosing is performed once per day starting on day 7 or day 13, and extending through day 16.

For determination of pulmonary eosinophilia, three days after the first OVA aerosol challenge (day 17), the mice are anesthetized with an i.p. injection of anesthetic (Ketamine/Acepromazine/Xylazine), and the tracheae is exposed and cannulated. The lungs and upper airways are lavaged twice with 0.5 ml of cold PBS. A portion (200 $\mu$l) of the bronchoalveolar lavage (BAL) fluid is enumerated using a Coulter counter Model ZB1 (Coulter Electronics, Hialeah, Fla.). The remaining BAL fluid is then centrifuged at 300×g for five minutes, and the cells are resuspended in 1 ml of HBSS (Gibco BRL) containing 0.5% fetal calf serum (HyClone) and 10 mM HEPES (Gibco BRL). The cell suspension is centrifuged in a cytospin (Shandon Southern Instruments, Sewickley, Pa.) and stained by Diff Quick (American Scientific Products, McGraw Park, Ill.) to differentiate BAL leukocytes into neutrophil, eosinophil, monocyte or lymphocyte subsets. The number of eosinophils in the BAL fluid is determined by multiplying the percentage of eosinophils by the total cell count.

Example 33
Caco-2 Cell Studies

Cell transport studies were conducted with Caco-2 cells grown on Snapwells between 22 to 28 days postseeding. Typically, 10 mM MES buffer (pH 6.5) with 5 mM KCl, 135 mM NaCl and 1.8 mM $CaCl_2$ was used for the apical side and 10 mM MOPS (pH 7.4) with 5 mM KCl, 132.5 mM NaCl and 1.8 mM $CaCl_2$ with 5 mM D-Glucose was used for the basolateral side. After washing the monolayers, appropriate buffers were pipetted into the respective chambers and the cells were pre-equilibrated at 37° C. for at least 15 min. On the day of the experiment the growth media was aspirated and the cell monolayers were preequilibrated with appropriate buffers at 37° C. for at least 15 min. Thereafter, TEER measurements were performed to confirm the integrity of the monolayers. Transepithelial flux measurements were made by mounting the cell monolayers in a side-by-side diffusion chamber system (Precision Instrument Design, Tahoe City, Calif.). Temperature was maintained at 37° C. with a circulating water jacket. The solutions were mixed with gas-lift circulation with 95% oxygen-5% carbon dioxide. Donor solutions with PD compounds, [$^{14}$C] mannitol (leakage marker) and [$^3$H] metoprolol (reference compound) were added to the apical chamber. Donor and receiver samples were collected at selected time intervals for up to 3 hours. Radiolabelled mannitol and metoprolol were analyzed using scintillation counting (TopCount, Packard Instruments, Downers Grove, Ill.). PD compounds were analyzed using a LC/MS/MS method. Apparent permeability coefficients were calculated using the following equation:

$$P_{app} = (V^* \, dC)/(A.C_O.dt)$$

where V=volume of the receiver solution in ml, A=surface area in $cm^2$, $C_O$=initial donor concentration in mM and dC/dt =change in the drug concentration in the receiver chamber over time.

Example 34

Metabolic Stability in Human and Rat Liver Microsomes

Compounds are individually incubated (5 μM, dissolved in DMSO) with human and rat liver microsomes (0.5 mg/mL protein) in 50 mM KHPO4 buffer at 37° C. in the presence of 1.0 mM NADPH. At 0, 10, 20 and 40 minutes, 100 μL aliquots are removed and added to 300 μL of acetonitrile. Standard curves are run in a similar manner with each compound at concentrations: 7.5 μM, 3.75 μM, 2.5 μM, 1.25 μM. The samples are analyzed for parent concentration by LC/MS/MS. The in vitro metabolic half-life determinations are determined from the concentration vs. time plots using WinNonlin. These in vitro data represent the rate of oxidative and hydrolytic metabolism.

F. OTHER EMBODIMENTS

From the above disclosure and examples, and from the claims below, the essential features of the invention are readily apparent. The scope of the invention also encompasses various modifications and adaptations within the knowledge of a person of ordinary skill. Examples include a disclosed compound modified by addition or removal of a protecting group, or an ester, pharmaceutical salt, hydrate, acid, or amide of a disclosed compound. Publications cited herein are hereby incorporated by reference in their entirety.

What is claimed is:
1. A compound of the following formula (I):

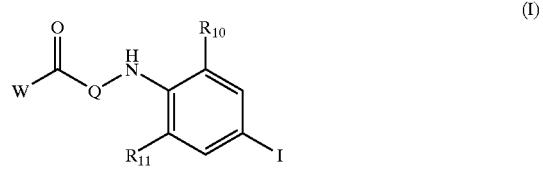

wherein

W is $OR_1$, $NR_2OR_1$, $NR_AR_B$, $NR_2NR_AR_B$, $O(CH_2)_{2-4}NR_AR_B$, or $NR_2(CH_2)_{2-4}NR_AR_B$;

$R_1$ is H, $C_{1-8}$ alkyl, $C_{3-8}$ alkenyl, $C_{3-8}$ alkynyl, $C_{3-8}$ cycloalkyl, phenyl, (phenyl)-$C_{1-4}$ alkyl, (phenyl)$C_{3-4}$ alkenyl, (phenyl)$C_{3-4}$ alkynyl, ($C_{3-8}$ cycloalkyl)$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical)$C_{1-4}$ alkyl, ($C_{3-8}$ heterocyclic radical)-$C_{3-4}$ alkenyl, ($C_{3-8}$ heterocyclic radical)$C_{3-4}$ alkynyl or $(CH_2)_{2-4}NR_CR_D$;

$R_2$ is H, $C_{1-4}$ alkyl, phenyl, $C_{3-6}$ cycloalkyl, $C_{3-6}$ heterocyclic radical, or ($C_{3-6}$ cycloalkyl)methyl;

$R_A$ is H, $C_{1-6}$ alkyl, $C_{3-8}$ alkenyl, $C_{3-8}$ alkynyl, $C_{3-8}$ cycloalkyl, phenyl, ($C_{3-8}$ cycloalkyl)$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical)$C_{1-4}$ alkyl, (aminosulfonyl)phenyl, [(aminosulfonyl)phenyl]$C_{1-4}$ alkyl, (aminosulfonyl)$C_{1-6}$ alkyl, (aminosulfonyl)$C_{3-6}$ cycloalkyl, [(aminosulfonyl)$C_{3-6}$ cycloalkyl]$C_{1-4}$ alkyl, or $(CH_2)_{2-4}NR_CR_D$;

$R_B$ is H, $C_{1-8}$ alkyl, $C_{3-8}$ alkenyl, $C_{3-8}$ alkynyl, $C_{3-8}$ cycloalkyl, or phenyl;

Q is one of the following formulae (i)–(iii):

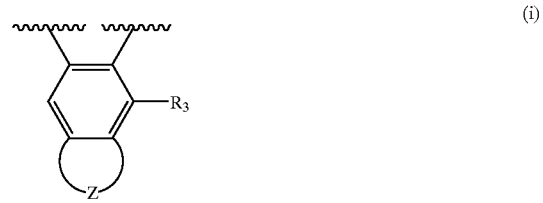

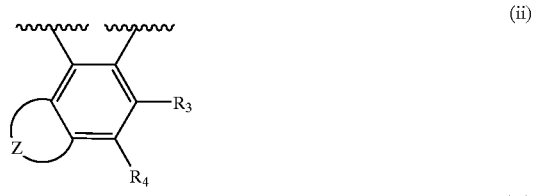

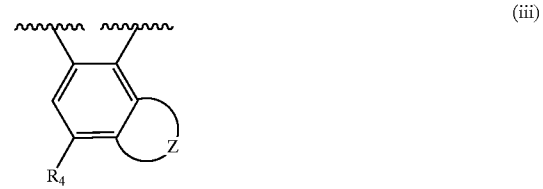

$R_3$ is H or F;
$R_4$ is halo, $NO_2$, $SO_2NR_O(CH_2)_{2-4}NR_ER_F$, $SO_2NR_ER_F$, or (CO)T;
T is $C_{1-8}$ alkyl, $C_{3-8}$ cycloalkyl, $(NR_ER_F)C_{1-4}$ alkyl, $OR_F$, —$NR_O(CH_2)_{2-4}NR_ER_F$, or $NR_ER_F$;

Z is one of the following formulae (iv)–(viii):

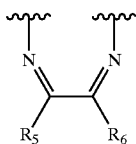 (iv)

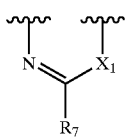 (v)

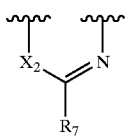 (vi)

one of $R_5$ and $R_6$ is H or methyl and the other of $R_5$ and $R_6$ is H, $C_{1-6}$ alkyl, $C_{2-6}$ alkenyl, $C_{2-6}$

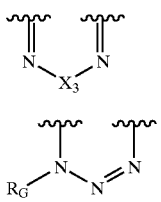 (vii)

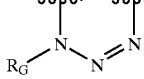 (viii)

alkynyl, phenyl, benzyl, or —M—E—G;

M is O, CO, $SO_2$, $NR_J$, $(CO)NR_H$, $NR_H(CO)$, $NR_H(SO_2)$, $(SO_2)NR_H$, or $CH_2$;

E is $(CH_2)_{1-4}$ or $(CH_2)_mO(CH_2)_p$ where $1 \leq$ (each of m and p)$\leq 3$ and $2 \leq (m+p) \leq 4$; or E is absent;

G is $R_K$, $OR_I$ or $NR_JR_K$, provided that if p=1, then G is H;

$R_7$ is H, $C_{1-4}$ alkyl, $C_{2-4}$ alkenyl, $C_{2-4}$ alkynyl, $C_{3-6}$ cycloalkyl, phenyl, 2-pyridyl, 3-pyridyl, 4-pyridyl, $(CH_2)_{1-2}Ar$, where Ar is phenyl, 2-pyridyl, 3-pyridyl, or 4-pyridyl, $SO_2NR_H(CH_2)_{2-4}NR_JR_K$, $(CO)(CH_2)_{2-4}NR_JR_K$ or $(CO)NR_H(CH_2)_{2-4}NR_JR_K$;

$X_1$ is O, S, $NR_8$, or $CHR_9$; $X_2$ is O, S, or $CHR_9$; and $X_3$ is O or S; where if $X_1$ or $X_2$ $CHR_9$, said compound may also be a tautomerized indole;

$R_8$ is H, $C_{1-4}$ alkyl, phenyl, 2-pyridyl, 3-pyridyl, 4-pyridyl, $(CH_2)_{1-2}Ar$, where Ar is phenyl, 2-pyridyl, 3-pyridyl, or 4-pyridyl, $C_{2-4}$ alkenyl, $C_{2-4}$ alkynyl, $C_{3-6}$ cycloalkyl, or $(C_{2-4}$ alkyl)$NR_LR_M$; provided $R_7$ and $R_8$ together have no more than 14 carbon atoms, exclusive of $R_L$, $R_M$, $R_J$ and $R_K$;

$R_G$ is hydrogen, $C_{1-4}$ alkyl, phenyl, 2-pyridyl, 3-pyridyl, 4-pyridyl, $C_{3-4}$ alkenyl, $C_{3-4}$ alkynyl, $C_{3-6}$ cycloalkyl, $(CO)OR_P$, $(C_{2-4}$ alkyl)$NR_LR_M$, $(CO)NR_N(CH_2)_{2-4}NR_LR_M$, $(CO)NR_LR_M$, $(CO)(CH_2)_{2-4}$—$NR_LR_M$, or $(CH_2)_{1-2}Ar$, where Ar is phenyl, 2-pyridyl, 3-pyridyl, or 4-pyridyl;

$R_9$ is $C_{1-4}$ alkyl, phenyl, 2-pyridyl, 3-pyridyl, 4-pyridyl, $C_{2-4}$ alkenyl, $C_{2-4}$ alkynyl, $C_{3-6}$ cycloalkyl, $(CO)OR_P$, $(C_{2-4}$ alkyl)$NR_LR_M$, $(CO)NR_N(CH_2)_{2-4}NR_LR_M$, $(CO)NR_LR_M$, $(CO)(CH_2)_{2-4}$—$NR_LR_M$, or $(CH_2)_{1-2}Ar'$, where Ar' is phenyl, 2-pyridyl, 3-pyridyl, or 4-pyridyl;

$R_P$ is H, $C_{1-6}$ alkyl, phenyl, $C_{3-4}$ alkenyl, $C_{3-4}$ alkynyl, $C_{3-6}$ cycloalkyl, or $(CH_2)_{2-4}NR_LR_M$;

$R_{10}$ is H, methyl, halo, or $NO_2$;

$R_{11}$ is H, methyl, halo, or $NO_2$;

each of $R_C$, $R_D$, $R_E$, $R_F$, $R_I$, $R_J$, $R_K$, $R_L$ and $R_M$ is independently selected from H, $C_{1-4}$ alkyl, $C_{3-4}$ alkenyl, $C_{3-4}$ alkynyl, $C_{3-6}$ cycloalkyl, and phenyl; each of $NR_CR_D$, $NR_ER_F$, $NR_JR_K$, and $NR_LR_M$ can also independently be morpholinyl, piperazinyl, pyrrolidinyl, or piperadinyl; and each of $R_H$, $R_N$, and $R_O$ is independently H, methyl, or ethyl;

wherein each hydrocarbon radical or heterocyclic radical above is optionally substituted with between 1 and 3 substituents independently selected from halo, $C_{1-4}$ alkyl, $C_{3-6}$ cycloalkyl, $C_{3-4}$ alkenyl, $C_{3-4}$ alkynyl, phenyl, hydroxyl, amino, (amino)sulfonyl, and $NO_2$, wherein each substituent alkyl, cycloalkyl, alkenyl, alkynyl or phenyl is in turn optionally substituted with between 1 and 3 substituents independently selected from halo, $C_{1-2}$ alkyl, hydroxyl, amino, and $NO_2$;

or a pharmaceutically acceptable salt or $C_{1-7}$ ester thereof.

2. A compound of claim 1, wherein Q is formula (i).

3. A compound of claim 2, wherein $R_3$ is H or fluoro.

4. A compound of claim 3, wherein $R_4$ is fluoro, chloro, or bromo.

5. A compound of claim 1, wherein $R_{10}$ is hydrogen, methyl, fluoro, or chloro.

6. A compound of claim 1, wherein $R_{11}$ is methyl, chloro, fluoro, nitro, or hydrogen.

7. A compound of claim 6, wherein $R_{11}$ is H.

8. A compound of claim 6, wherein $R_{11}$ is fluoro.

9. A compound of claim 5, wherein each of $R_{10}$ and $R_{11}$ is fluoro.

10. A compound of claim 1, wherein $R_1$ is H, methyl, ethyl, propyl, isopropyl, isobutyl, benzyl, phenethyl, allyl, $C_{3-5}$ alkenyl, $C_{3-6}$ cycloalkyl, $(C_{3-5}$ cycloalkyl)$C_{1-2}$ alkyl, $(C_{3-5}$ heterocyclic radical)$C_{1-2}$ alkyl, or $(CH_2)_{2-4}NR_CR_D$.

11. A compound of claim 10, wherein $R_1$ is H or $(C_{3-4}$ cycloalkyl)$C_{1-2}$ alkyl.

12. A compound of claim 1, wherein $R_2$ is H or methyl.

13. A compound of claim 1, wherein $R_A$ has at least one hydroxyl substituent.

14. A compound of claim 1, wherein $R_A$ is H, methyl, ethyl, isobutyl, hydroxyethyl, phenyl, 2-piperidin-1-yl-ethyl, 2,3-dihydroxy-propyl, 3-[4-(2-hydroxyethyl)-piperazin-1-yl]-propyl, 2-pyrrolidin-1-yl-ethyl, or 2-diethylamino-ethyl; and $R_B$ is H; or where $R_B$ is methyl and $R_A$ is phenyl.

15. A compound of claim 1, wherein W is $NR_AR_B$ or $NR_2NR_AR_B$.

16. A compound of claim 1, wherein W is $NR_2(CH_2)_{2-4}NR_AR_B$ or $O(CH_2)_{2-3}NR_AR_B$.

17. A compound of claim 1, wherein W is $NR_2OR_1$.

18. A compound of claim 1, wherein W is $OR_1$.

19. A compound of claim 1, wherein Z is formula (v).

20. A compound of claim 19, wherein $X_1$ is $NR_8$, and $R_7$ is H.

21. A compound of claim 1 having the structure 7-fluoro-6-(4-iodo-2-methyl-phenylamino)-1H-benzoimidazole-5-carboxylic acid.

22. A compound of claim 1 selected from 7-fluoro-6-(4-iodo-2-methyl -phenylamino)-1H-benzoimidazole-5- carboxylic acid; 7-fluoro-6-(4-iodo-2-methyl-phenylamino)-benzooxazole-5-carboxylic acid; 7-fluoro-6-(4-iodo-2-methyl-phenylamino)-benzothiazole-5-carboxylic acid; 7-fluoro-6-(4-iodo-2-methyl-phenylamino)-benzo[1,2,5]thiadiazole-5-carboxylic acid; 7-fluoro-6-(4-iodo-2-methyl-phenylamino)-benzo[1,2,5]oxadiazole-5-carboxylic acid; 7-fluoro-6-(4-iodo-2-methyl-phenylamino)-2-(2-hydroxyethyl)-1H-benzoimidazole-5-carboxylic acid; 7-fluoro-6-(4-iodo-2-methyl-phenylamino)-2-(2-dimethylamino-ethyl)-1H-benzoimidazole-5-carboxylic acid; 7-fluoro-6-(4-iodo-2-methyl-phenylamino)-1-acetyl-benzoimidazole-5-carboxylic acid; 8-fluoro-7-(4-iodo-2-methyl-phenylamino)-quinoxaline-6-carboxylic acid; and 7-fluoro-6-(4-iodo-2-methyl-phenylamino)-1H-benzotriazole-5-carboxylic acid; and the corresponding hydroxamic acids and cyclopropylmethyl hydroxamates.

23. A pharmaceutical composition comprising a compound of claim 1 and a pharmaceutically-acceptable carrier.

24. A method for treating a proliferative disease, said method comprising administering to a patient in need of such treatment a pharmaceutically-effective amount of a composition comprising a compound of claim 1.

25. A method of claim 24, wherein said proliferative disease is selected from psoriasis, restenosis, autoimmune disease, and atherosclerosis.

26. A method for treating cancer, said method comprising administering to a patient in need of such treatment a pharmaceutically-effective amount of a composition comprising a compound of claim 1.

27. A method of claim 26, wherein said cancer is MEK-related.

28. A method of claim 26, wherein said cancer is colorectal, cervical, breast, ovarian, brain, acute leukemia, gastric, non-small cell lung, pancreatic or renal cancer.

29. A method for treating, or ameliorating the sequelae of, a stroke, said method comprising administering to a patient in need of such treatment a pharmaceutically-effective amount of a composition comprising a compound of claim 1.

30. A method for treating, or ameliorating the sequelae of, heart failure, said method comprising administering to a patient in need of such treatment a pharmaceutically-effective amount of a composition comprising a compound of claim 1.

31. A method for treating or reducing the symptoms of xenograft rejection, said method comprising administering to an organ transplant, limb transplant, cell transplant, skin transplant, or bone marrow transplant patient a pharmaceutically-effective amount of a composition comprising a compound of claim 1.

32. A method for treating osteoarthritis, said method comprising administering to a patient in need of such treatment a pharmaceutically-effective amount of a composition comprising a compound of claim 1.

33. A method for treating rheumatoid arthritis, said method comprising administering to a patient in need of such treatment a pharmaceutically-effective amount of a composition comprising a compound of claim 1.

34. A method for treating a viral infection, said method comprising administering to a patient in need of such treatment a pharmaceutically-effective amount of a composition comprising a compound of claim 1.

35. A method for treating cystic fibrosis, said method comprising administering to a patient in need of such treatment a pharmaceutically-effective amount of a composition comprising a compound of claim 1.

36. A method for treating hepatomegaly, said method comprising administering to a patient in need of such treatment a pharmaceutically-effective amount of a composition comprising a compound of claim 1.

37. A method for treating cardiomegaly, said method comprising administering to a patient in need of such treatment a pharmaceutically-effective amount of a composition comprising a compound of claim 1.

38. A method for treating Alzheimer's disease, said method comprising administering to a patient in need of such treatment a pharmaceutically-effective amount of a composition comprising a compound of claim 1.

39. A method for treating a complication of diabetes, said method comprising administering to a patient in need of such treatment a pharmaceutically-effective amount of a composition comprising a compound of claim 1.

40. A method for treating septic shock, said method comprising administering to a patient in need of such treatment a pharmaceutically-effective amount of a composition comprising a compound of claim 1.

41. A method for treating asthma, said method comprising administering to a patient in need of such treatment a pharmaceutically-effective amount of a composition comprising a compound of claim 1.

42. A method for treating cancer, said method comprising (a) administering to a patient in need of such treatment, a pharmaceutically-effective amount of a composition comprising a compound of claim 1; and (b) administering a therapy selected from radiation therapy and chemotherapy.

43. A method of claim 42, wherein said chemotherapy comprises a mitotic inhibitor.

44. A method of claim 43, wherein said chemotherapy comprises a mitotic inhibitor selected from paclitaxel, docetaxel, vincristine, vinblastine, vinorelbine, and vinflunine.

* * * * *